(12) United States Patent
Breyen et al.

(10) Patent No.: US 6,678,559 B1
(45) Date of Patent: Jan. 13, 2004

(54) IMPLANTABLE MEDICAL DEVICE HAVING A CAPACITOR ASSEMBLY WITH LINER

(75) Inventors: Mark D. Breyen, Plymouth, MN (US); Dan C. Haeg, Champlin, MN (US); Andrew M. Jacobs, Eden Prairie, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/531,352

(22) Filed: Mar. 20, 2000

Related U.S. Application Data

(60) Provisional application No. 60/125,688, filed on Mar. 23, 1999.

(51) Int. Cl.⁷ .................................................. A61N 1/18
(52) U.S. Cl. ............................................ 607/5; 361/503
(58) Field of Search .............................. 607/5; 361/503

(56) References Cited

U.S. PATENT DOCUMENTS

| | | | |
|---|---|---|---|
| 3,555,369 A | 1/1971 | Yoshino | 317/230 |
| 3,738,370 A | 6/1973 | Charms | 128/419 D |
| RE27,757 E | 9/1973 | Mirowski | 128/419 D |
| 3,883,784 A | 5/1975 | Peck et al. | 317/258 |
| 3,888,260 A | 6/1975 | Fischell | 128/419 PG |
| 4,030,509 A | 6/1977 | Heilman et al. | 128/419 D |
| 4,253,466 A | 3/1981 | Hartlaub et al. | 128/419 PG |
| 4,254,775 A | 3/1981 | Langer | 128/419 D |
| 4,374,817 A | 2/1983 | Lehman et al. | 423/319 |
| 4,375,817 A | 3/1983 | Engle et al. | 128/419 D |
| 4,379,459 A | 4/1983 | Stein | 128/419 PG |
| 4,384,585 A | 5/1983 | Zipes | 128/719 D |
| 4,476,868 A | 10/1984 | Thompson | 128/419 PG |
| 4,556,063 A | 12/1985 | Thompson et al. | 128/419 PT |
| 4,577,633 A | 3/1986 | Berkovits et al. | 128/419 D |
| 4,587,970 A | 5/1986 | Holley et al. | 128/419 PG |
| 4,693,253 A | 9/1987 | Adams | 128/419 D |
| 4,726,380 A | 2/1988 | Vollmann et al. | 128/419 PG |
| 4,821,723 A | 4/1989 | Baker, Jr. et al. | 128/419 D |

(List continued on next page.)

OTHER PUBLICATIONS

Lunsmann, Paul, and Douglas R. MacFarlane, "High Energy Density Capacitors for Implantable Defibrillators", Carts 96: 16$^{th}$ Capacitor and Resistor Technology Symposium, Mar. 11–15, 1996, pp. 277–280.

Troup, M.D., Paul J. "Implantable Cardioverters and Defibrillators" *Current Problems in Cardiology*, XIV (12):673–815. Dec. 1989.

Zipes, LT. CDR. Douglas P., M.C., USNR, "Arrhythmias" *The Clinical Application of Cardioversion* pp. 239–260.

*Primary Examiner*—Mark Bockelman
(74) *Attorney, Agent, or Firm*—Girma Wolde-Michael; Daniel G. Chapik

(57) ABSTRACT

An implantable medical device comprising a housing, a capacitor assembly, an electronics module and an energy source, such as a battery. The capacitor assembly is disposed within the housing. The electronics module is electrically connected to the capacitor assembly and similarly disposed within the housing. The capacitor assembly comprising a case, an electrode stack and an insulative liner between the case and the electrode stack. The capacitor assembly electrode stack comprising a plurality of electrode subassemblies each having a plurality of anode plates and a plurality of cathode plates with a separation layer between anode and cathode plates. The liner also maintains alignment and immobilizes the electrode stack within the capacitor assembly. Finally, the energy source is electrically connected to the electronics module. With this configuration, an overall shape and size of the implantable medical device is optimized. Methods for assembling an implantable medical device and for forming the capacitor assembly insulative liner are provided.

34 Claims, 22 Drawing Sheets

U.S. PATENT DOCUMENTS

| | | | |
|---|---|---|---|
| 4,880,005 A | 11/1989 | Pless et al. | 128/419 PG |
| 4,942,501 A | 7/1990 | MacFarlane et al. | 361/523 |
| 4,949,719 A | 8/1990 | Pless et al. | 128/419 D |
| 4,964,877 A | 10/1990 | Keister et al. | 29/623.1 |
| 5,131,388 A | 7/1992 | Pless et al. | 128/419 D |
| 5,146,391 A | 9/1992 | MacFarlane et al. | 361/525 |
| 5,147,737 A | 9/1992 | Post et al. | 429/94 |
| 5,153,820 A | 10/1992 | MacFarlane et al. | 361/525 |
| 5,188,105 A | 2/1993 | Keimel | 128/419 D |
| 5,250,373 A | 10/1993 | Muffoletto et al. | 429/161 |
| 5,312,453 A | 5/1994 | Shelton et al. | 607/19 |
| 5,312,458 A | 5/1994 | Muffoletto et al. | 29/623.1 |
| 5,314,430 A | 5/1994 | Bardy | 607/5 |
| 5,336,253 A | 8/1994 | Gordon et al. | 607/122 |
| 5,354,316 A | 10/1994 | Keimel | 607/15 |
| 5,383,909 A | 1/1995 | Keimel | 607/7 |
| 5,411,537 A | 5/1995 | Munshi et al. | 607/33 |
| 5,434,017 A | 7/1995 | Berkowitz et al. | 429/94 |
| 5,439,760 A | 8/1995 | Howard et al. | 429/94 |
| 5,447,519 A | 9/1995 | Peterson | 607/5 |
| 5,468,569 A | 11/1995 | Pyszczek et al. | 429/94 |
| 5,522,851 A | 6/1996 | Fayram | 607/5 |
| 5,545,186 A | 8/1996 | Olson et al. | 607/14 |
| 5,549,717 A | 8/1996 | Takeuchi et al. | 29/623.2 |
| 5,584,890 A | 12/1996 | MacFarlane et al. | 29/25.03 |
| 5,591,212 A | 1/1997 | Keimel | 607/5 |
| 5,628,801 A | 5/1997 | MacFarlane et al. | 29/25.03 |
| 6,042,624 A | 3/2000 | Breyen et al. | 29/25.03 |
| 6,388,866 B1 * | 5/2002 | Rorvick et al. | 361/503 |

* cited by examiner

IMPLANTABLE MEDICAL DEVICE HAVING A CAPACITOR ASSEMBLY WITH LINER

RELATED APPLICATION

This Non-Provisional Utility Patent Application claims priority and other benefits from U.S. Provisional Patent Application Ser. No. 60/125,688 filed Mar. 23, 1999 entitled "Case Liner for Use in Flat Aluminum Electrolytic Capacitor."

FIELD OF THE INVENTION

This invention relates to implantable medical devices such as defibrillators and automatic implantable defibrillators (AIDs), and their various components. More particularly, it relates to an implantable medical device including a flat capacitor with case liner configured to optimize an overall size and shape of the device.

BACKGROUND OF THE INVENTION

Implantable medical devices (IMDs) for therapeutic stimulation of the heart are well known in the art. Examples of various forms of IMDs and their respective functions include: a programmable demand pacemaker disclosed in U.S. Pat. No. 4,253,466 issued to Hartlaub et al. to deliver electrical energy, typically ranging in magnitude between about 5 and about 25 micro Joules, to the heart to initiate the depolarization of cardiac tissue to treat the heart by providing pacemaker spike in the absence of naturally occurring spontaneous cardiac depolarizations; an automatic implantable defibrillator (AID), such as those described in U.S. Pat. No. Re. 27,757 to Mirowski et al. and U.S. Pat. No. 4,030,509 to Heilman et al., deliver a nonsynchronous high-voltage energy pulse (about 40 Joules) to the heart to interrupt ventricular fibrillation through widely spaced electrodes located outside of the heart, thus mimicking transthoracic defibrillation; a pacemaker/cardioverter/defibrillator (PCD) disclosed in U.S. Pat. No. 4,375,817 to Engle et al., to detect the onset and progression of tachyarrhythmia so that progressively greater energy levels may be applied to the heart to interrupt a ventricular tachycardia or fibrillation; an external synchronized cardioverter, such as that described in "Clinical Application of Cardioversion" in Cardiovascular Clinics, 1970, Vol. 2, pp. 239–260 by Douglas P. Zipes, provides cardioversion shocks synchronized with ventricular depolarization to ensure that the cardioverting energy is not delivered during the vulnerable T-wave portion of the cardiac cycle; an implantable cardioverter, such as those disclosed in U.S. Pat. No. 4,384,585 to Douglas P. Zipes and in U.S. Pat. No. 3,738,370 to Charms, detect the intrinsic depolarizations of cardiac tissue and pulse generator circuitry delivers moderate energy level stimuli (in the range of about 0.1 to about 10 Joules) to the heart synchronously with the detected cardiac activity.

An IMD consists generally of a sealed housing maintaining a capacitor(s), an electronics module(s) and an energy source. The electronics module normally includes a circuit board maintaining a variety of electrical components designed, for example, to perform sensing and monitoring functions or routines, as well as to accumulate data related to IMD operation. The electronics module is electrically connected to the capacitor and the power source such that amongst other functions, the electronics module causes the power source to charge and recharge the capacitor. To satisfy power and safety requirements, the power source typically consists of two series-connected batteries. So as to optimize volumetric efficiency, the batteries are typically formed to assume a cube-like shape. For example, a well accepted IMD configuration includes two, three-volt cube-like batteries connected in series.

Typically, the electrical energy required to power an implantable cardiac pacemaker is supplied by a low voltage, low current drain, long-lived power source such as a lithium iodine pacemaker battery of the type manufactured by Wilson Greatbatch, Ltd. or Medtronic, Inc. While the energy density of such power sources is typically relatively high, they are generally not capable of being rapidly and repeatedly discharged at high current drains in the manner required to directly cardiovert the heart with cardioversion energies in the range of 0.1 to 10 Joules. Moreover, the nominal voltage at which such batteries operate is generally too low for cardioversion applications. Higher energy density battery systems are known which can be more rapidly or more often discharged, such as lithium thionyl chloride power sources. Neither of the foregoing battery types, however, may have the capacity or the voltage required to provide an impulse of the required magnitude on a repeatable basis to the heart following the onset of tachyarrhythmia.

Generally speaking, it is necessary to employ a DC-DC converter to convert electrical energy from a low voltage, low current power supply to a high voltage energy level stored in a high-energy storage capacitor. Charging of the high-energy capacitor is accomplished by inducing a voltage in the primary winding of a transformer creating a magnetic field in the secondary winding. When the current in the primary winding is interrupted, the collapsing field develops a current in the secondary winding which is applied to the high-energy capacitor to charge it. The repeated interruption of the supply current charges the high-energy capacitor to a desired level over time.

Energy, volume, thickness and mass are critical features in the design of IMDs. IMDs typically have a volume of about 40 to about 60 cc, a thickness of about 13 mm to about 16 mm and a mass of approximately 100 grams. One of the components important to optimization of those features is the high voltage capacitor used to store the energy required for defibrillation. Such capacitor a typically deliver energy in the range of about 25 to 40 Joules.

It is desirable to reduce the volume, thickness and mass of such capacitors and devices without reducing deliverable energy. Doing so is beneficial to patient comfort and minimizes complications due to erosion of tissue around the device. Reductions in size of the capacitors may also allow for the balanced addition of volume to the battery, thereby increasing longevity of the device, or balanced addition of new components, thereby adding functionality to the device. It is also desirable to provide such devices at low cost while retaining the highest level of performance.

Most conventional IMDs employ commercial photoflash capacitors similar to those described by Troup in "Implantable Cardioverters and Defibrillators," Current Problems in Cardiology, Volume XIV, Number 12, December 1989, Year Book Medical Publishers, Chicago, and U.S. Pat. No. 4,254,775 for "Implantable Defibrillator and Package Therefor." The electrodes in such capacitors are typically spirally wound to form a coiled electrode assembly. Most commercial photoflash capacitors contain a core of separator paper intended to prevent brittle anode foils from fracturing during coiling. The anode, cathode and separator are typically wound around such a paper core. The core limits both the thinness and volume of the IMDs in which they are placed. The cylindrical shape of commercial photoflash capacitors also limits the volumetric packaging efficiency and thickness of an IMD made using same.

Recently developed flat aluminum electrolytic capacitors have overcome some disadvantages inherent in commercial cylindrical capacitors. For example, U.S. Pat. No. 5,131,388 to Pless et al. discloses a relatively volumetrically efficient flat capacitor having a plurality of planar layers arranged in a stack. Each layer contains an anode layer, a cathode layer and means for separating the anode layers and cathode layers (such as paper). The anode layers and the cathode layers are electrically connected in parallel.

A segment of today's IMD market employs flat capacitors to overcome some of the packaging and volume disadvantages associated with cylindrical photoflash capacitors. Examples of such flat capacitors are described in the '388 patent to Pless et al. for "Implantable Cardiac Defibrillator with Improved Capacitors," and in U.S. Pat. No. 5,522,851 to Fayram for "Capacitor for an Implantable Cardiac Defibrillators." Additionally, flat capacitors are described in a paper entitled "High Energy Density Capacitors for Implantable Defibrillators" by P. Lunsmann and D. MacFarlane presented at the 16th Capacitor and Resistor Technology Symposium.

Numerous efforts have been made to improve upon the size, shape and performance characteristics of the various IMD components. For example, implementation of a flat capacitor configuration has greatly improved IMD performance as well as reducing and improving the size and shape of the IMD housing. Similarly, advancements in electrical component technology has greatly reduced size requirements associated with the electronics module, along with facilitating use of a lower voltage power source (e.g., three-volt versus six-volt). Along these same lines, enhancements in materials and construction techniques used for IMD batteries have resulted in the reduction of sizes and costs.

A flat aluminum electrolytic capacitor stack is built as descried in earlier disclosures. Commercially available cylindrical capacitors as well as flat aluminum electrolytic capacitors described in prior art patents such as '851 Pless et al. typically employ the use of a metal housing, such as aluminum or an aluminum alloy. Electrical insulation from the cathode elements is not employed. Electrical isolation from the anode elements is typically employed by using separator elements (e.g., a paper layer) that overhang the edges of the electrode plates, thereby separating the anode electrode elements from the metal case. The case is either directly connected to the cathode elements through a welded joint or through contact with the electrolyte.

Reducing the size of aluminum electrolytic capacitors, while at the same time increasing the energy storage capacity per unit volume or energy density requires the minimization of non-energy storage elements. One way to reduce volume in flat aluminum electrolytic capacitors without reducing the amount of energy storage is to reduce or eliminate the length of paper that overhangs the edges of a flat capacitor stack. However, as this separator overhang is decreased the potential for contact between the edges of anode plates and the case wall increases. Close proximity may also result in arcing between the edges of the anode plates and the case wall at sufficient voltages. Elimination of separator overhang may also result in arcing between the edges of the anode plates and cathode plates.

A further problem with flat aluminum electrolytic capacitors that use a stacked plate type design is the relative movement of anode, cathode, and separator layers which may result in direct anode to cathode shorting paths or greater susceptibility to anode to case arcing. Use of alignment elements has been employed in the design of some conventional flat capacitors; however, these elements usually add inert volume on the order of 0.5 to 1.0 cc, while reducing the energy storage surface area of the anode/cathode. Yet another problem with conventional flat aluminum electrolytic capacitors is the incidental introduction of outer paper layers into the case-to-cover joint. This joint seal is conventionally formed by compression or weld. The presence of foreign material in the joint, such as separation layer paper, may result in a failed joint seal due to a blown weld or insufficient/leaky crimp rendering the capacitor assembly not fit for use.

To avoid the shortcomings of the above-discussed techniques and for other reasons presented in the Description of the Preferred Embodiments, a need exists for an IMD incorporating a capacitor having superior space-volumetric efficiencies to thereby advance the preferred objectives for continuing IMD size reduction, longer electrical IMD lifespan, higher reliability, lower cost and/or increased functionality.

SUMMARY OF THE INVENTION

One aspect of the present invention provides an implantable medical device including a housing, a capacitor assembly, an electronics module and an energy source, such as a substantially flat battery. The capacitor assembly is disposed within the housing. The electronics module is electrically connected to the capacitor assembly and is disposed within the housing. The energy source is electrically connected to the electronics module.

In one preferred embodiment of the present invention an insulative barrier such as a case liner is utilized in the capacitor assembly between the electrode stack and the conductive capacitor case element. Prior to being inserted into the case, a case liner element or elements is placed around the perimeter of the capacitor assembly electrode stack. The case liner provides the necessary insulation and isolation that allows for further reduction in separator overhang even to the level of no overhang.

In one embodiment, the capacitor assembly electrode stack is first inserted into the case and a case liner slid into place around the capacitor assembly electrode stack. In another embodiment, the liner is first placed inside of the case and the capacitor assembly electrode stack is either inserted into the case liner or the electrode stack may be constructed directly into the liner. The capacitor assembly case liner aligns and immobilizes the capacitor assembly electrode stack. The capacitor assembly liner is especially effective in reducing shifting of the electrode stack upon insertion into the case. The liner design may be realized in many different preferred embodiments, including two-piece construction. The capacitor assembly case liner may separate into two pieces along one of any of the three dimensions. For example, the capacitor assembly case liner may consist of top and bottom portions, left and right portions, or front and back portions. Alternatively, the capacitor assembly case liner is formed as a box having one hinged side. In another embodiment, the capacitor assembly case liner is a single piece construction folded around the capacitor assembly electrode stack. The liner may be constructed of a variety of insulative materials, and by a variety of methods. A preferred method uses a thermo-forming technique. Alternatively, the liner may be machined, injection molded, or thin film coated onto the capacitor assembly case.

BRIEF DESCRIPTION OF THE DRAWINGS

Reference is now made to the accompanying detailed drawings of the preferred embodiments in which like reference numerals represent like or similar parts throughout, wherein.

DETAILED DESCRIPTION OF THE PREFERRED EMBODIMENTS

The present invention provides an implantable medical device (IMD) having a substantially flat capacitor assembly includes an insulative (i.e., electrically non-conductive) barrier placed between the electrode stack and the conductive capacitor assembly case. The unique assembly according to the present invention reduces or eliminates the amount of anode/cathode separation layer overhang, thus reducing the distance necessary between the capacitor assembly electrode stack and the conductive capacitor assembly case. As a result, overall capacitor assembly size is reduced or, alternatively, anode/cathode subassembly size can be increased (i.e., maximized) providing additional energy storage capability.

Figure 1:
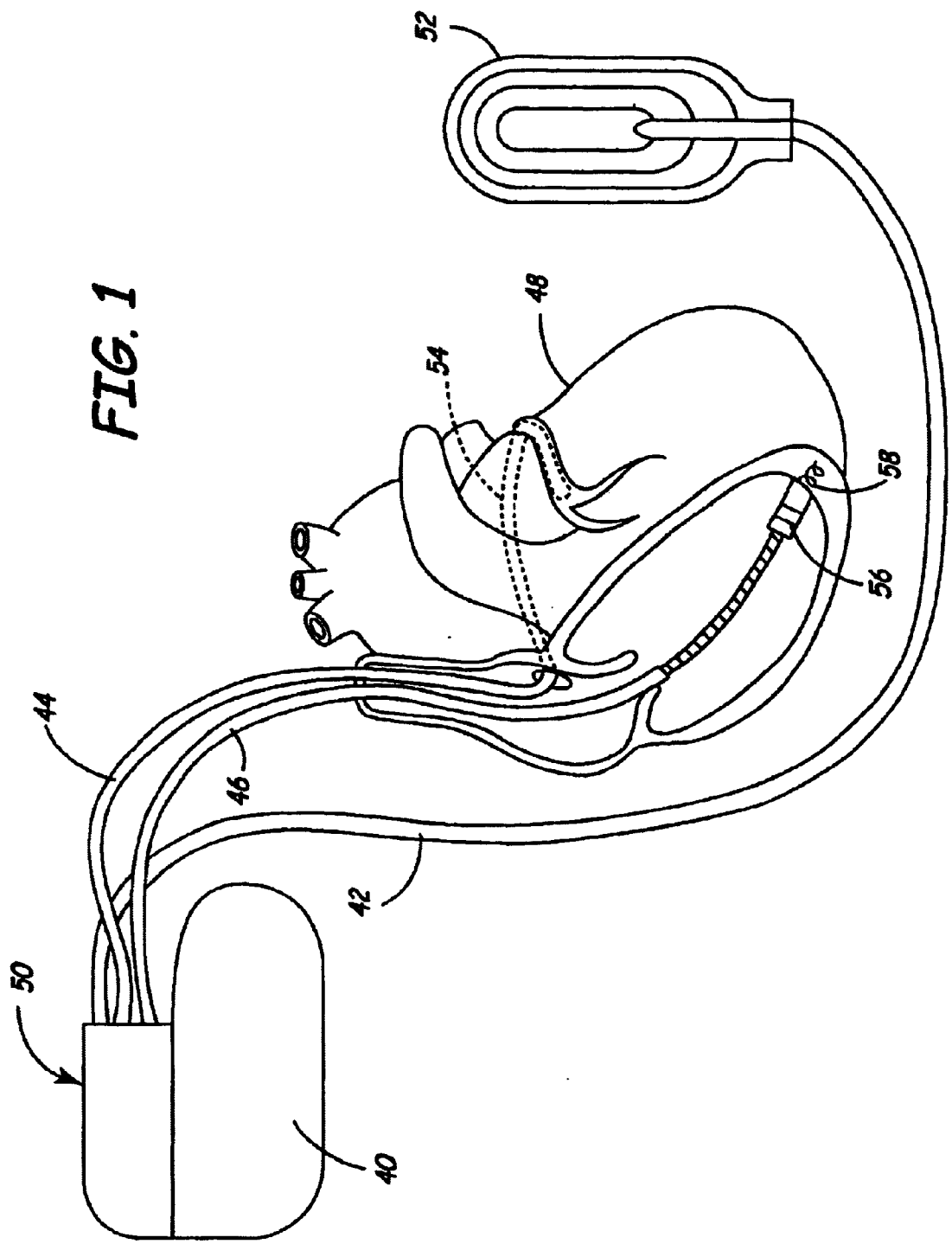
FIG. 1 illustrates the physical components of one embodiment of an implantable medical device (IMD) having a capacitor assembly with insulative barrier, and lead system of one embodiment of the present invention.

FIG. 1 illustrates one embodiment of an IMD 40 of the present invention, its associated electrical leads 42, 44 and 46, and their relationship to a human heart 48. The leads are coupled to IMD 40 by means of multi-port connector block 50, which contains separate connector ports for each of the three leads illustrated. Lead 42 is coupled to subcutaneous electrode 52, which is intended to be mounted subcutaneously in the region of the left chest. Lead 44 is a coronary sinus lead employing an elongated coil electrode, which is located in the coronary sinus and great vein region of the heart. The location of the electrode is illustrated in broken line format at 54, and extends around the heart from a point within the opening of the coronary sinus to a point in the vicinity of the left trial appendage.

Lead 46 is provided with elongated electrode coil 56, which is located in the right ventricle of the heart. Lead 46 also includes stimulation electrode 58 which takes the form of an advanceable helical coil which is screwed into the myocardial tissue of the right ventricle. Lead 46 may also include one or more additional electrodes for near and far field electrogram sensing.

In the system illustrated, cardiac pacing pulses are delivered between helical electrode 58 and elongated electrode 56. Electrodes 56 and 58 are also employed to sense electrical signals indicative of ventricular contractions. As illustrated, it is anticipated that the right ventricular electrode 56 will serve as the common electrode during sequential and simultaneous pulse multiple electrode defibrillation regimens. For example, during a simultaneous pulse defibrillation regimen, pulses would simultaneously be delivered between electrode 56 and electrode 52 and between electrode 56 and electrode 54. During sequential pulse defibrillation, it is envisioned that pulses would be delivered sequentially between subcutaneous electrode 52 and electrode 56 and between coronary sinus electrode 54 and right ventricular electrode 56. Single pulse, two electrode defibrillation pulse regimens may be also provided, typically between electrode 56 and coronary sinus electrode 54. Alternatively, single pulses may be delivered between electrodes 56 and 52.

Figure 2:
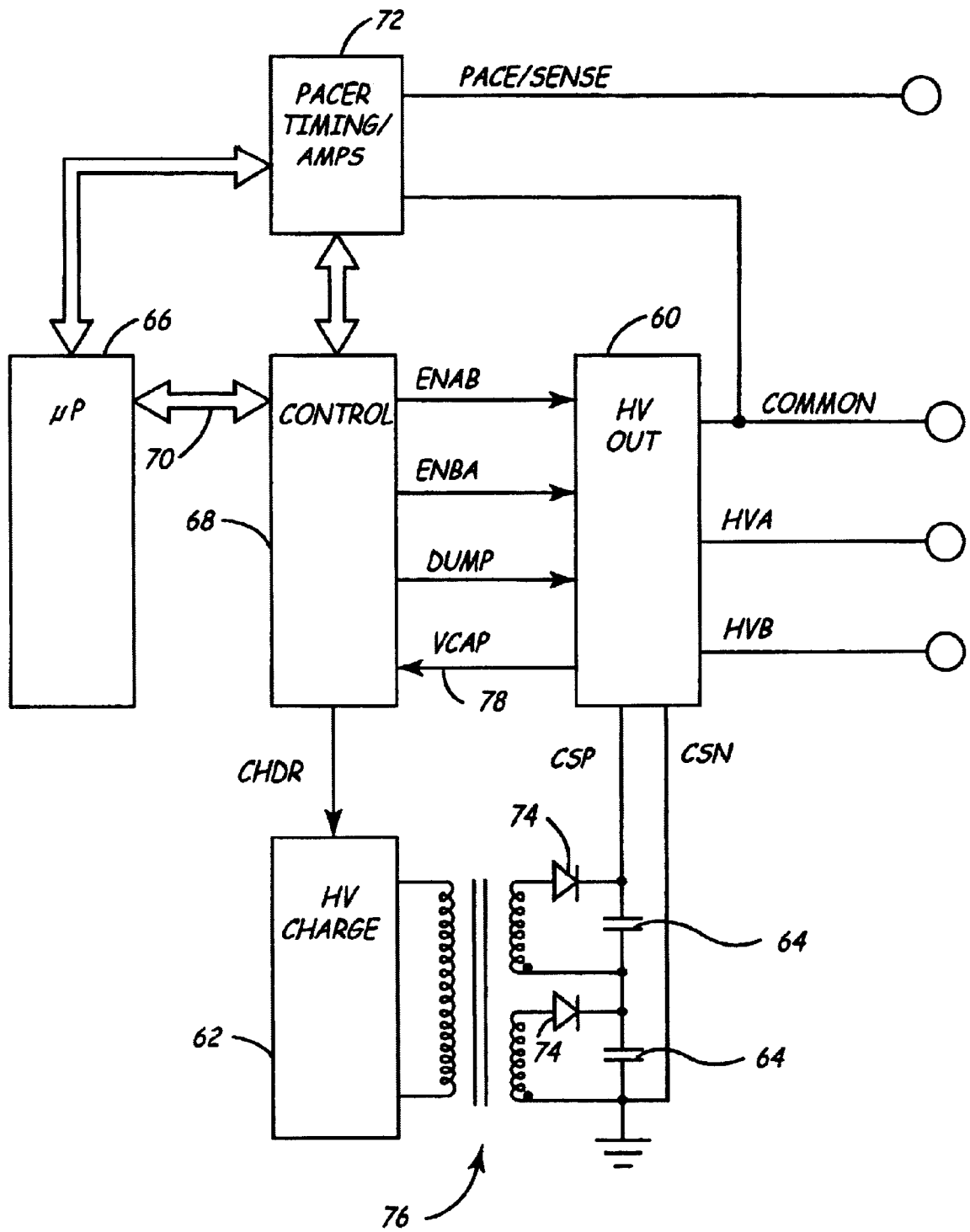
FIG. 2 is a block diagram illustrating the electrical coupling of the components within one embodiment of an IMD.

FIG. 2 is a block diagram illustrating the interconnection of high voltage output circuit 60, high voltage charging circuit 62 and capacitors 64 according to one embodiment of the present invention with an implantable pacemaker/cardioverter/defibrillator (PCD). As illustrated, the device is controlled by means of a stored program in microprocessor 66, which performs all necessary computational functions within the device. Microprocessor 66 is linked to control circuitry 68 by means of bidirectional data/control bus 70, and thereby controls operation of the output circuitry 60 and the high voltage charging circuitry 62. On reprogramming of the device or on the occurrence of signals indicative of delivery of cardiac pacing pulses or of the occurrence of cardiac contractions, pace/sense circuitry 72 will awaken microprocessor 66 to perform any necessary mathematical calculations, to perform tachycardia and fibrillation detection procedures and to update the time intervals controlled by the timers in pace/sense circuitry 72.

The basic operation of such a system in the context of an implantable PCD may correspond to any of the systems known in the art. More particularly, the flat aluminum electrolytic capacitor of the present invention may be employed generally in conjunction with various conventional systems, or in conjunction with the various systems or components disclosed in U.S. Pat. Nos. 4,693,253 to Adams, 5,188,105 to Keimel, 5,591,212 to Keimel, 5,383,909 to Keimel, 5,354,316 to Keimel, 5,336,253 to Gordon et al., 4,384,585 to Zipes, 4,949,719 to Pless et al., 4,374,817 to Engle et al., 4,577,633 to Berkowitz, 4,880,005 to Pless et al., 4,726,380 to Vollmann et al., 4,587,970 to Holley et al., 5,447,519 to Peterson, 4,476,868 to Thompson, 4,556,063 to Thompson, 4,379,459 to Stein, 5,312,453 to Wyborny, 5,545,186 to Olson, 5,345,316 to Keimel, 5,314,430 to Bardy, 5,131,388 to Pless, 3,888,260 to Fischell, 5,411,537 to Munshi et al. and 4,821,723 to Baker et al. All the foregoing patents are hereby incorporated herein by reference in their respective entireties.

The output circuitry of the present invention includes a capacitor bank comprising capacitor assemblies 64 and diodes 74, used for delivering defibrillation pulses to the electrodes. Alternatively, the capacitor bank may include a further set of capacitors. In FIG. 2, capacitors 64 are illustrated in conjunction with high voltage charging circuitry 62, controlled by the control/timing circuitry 68. As illustrated, capacitors 64 are charged by means of a high frequency, high voltage transformer 76. Proper charging polarities are maintained by means of the diodes 74. VCAP line 78 provides a signal indicative of the voltage on the capacitor bank, and allows for control of high voltage charging circuitry 62 and for termination of the charging function when the measured voltage equals the programmed charging level.

One suitable IMD for use with the present invention is disclosed in U.S. patent application Ser. No. 09/103,638, filed on Jun. 23, 1998 entitled, "METHOD OF MAKING AN IMPLANTABLE MEDICAL DEVICE HAVING A FLAT ELECTROLYTIC CAPACITOR" which is assigned to the assignee of the present application, and is herein incorporated by reference.

Figure 3A:
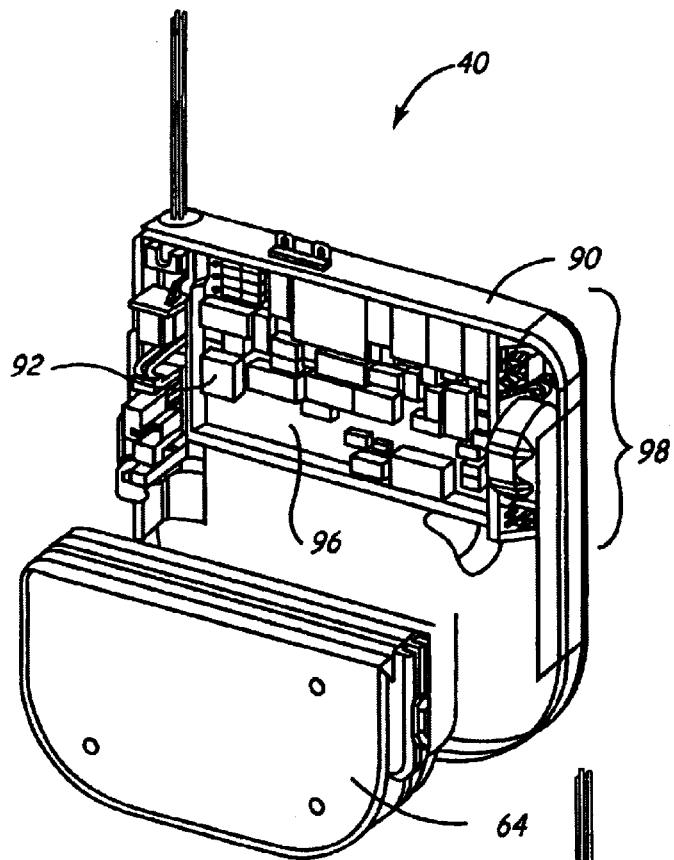
FIGS. 3(a) and 3(b) illustrate the configuration of components within one embodiment of an IMD.
Figure 3B:
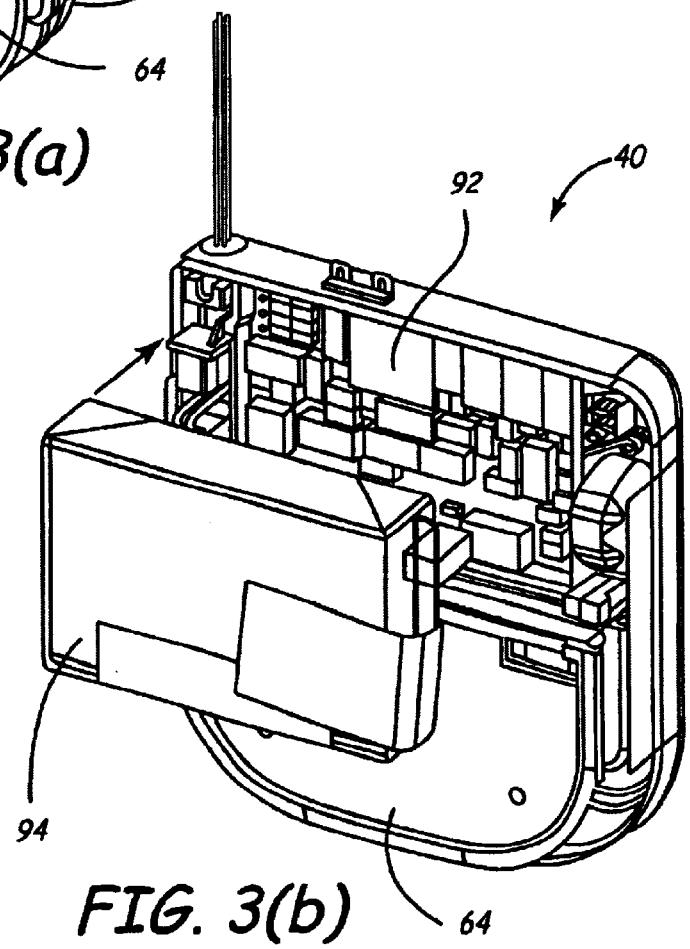

FIGS. 3(a) and 3(b) show perspective views of various components of IMD 40 of the present invention. IMD 40 includes housing 90, a capacitor assembly 64, an electronics module 92 and an energy source 94, such as a substantially flat battery. Electronics module 92 can assume a wide variety of forms and generally includes a circuit board 96 maintaining and interconnecting electrical components 98. The exact composition of electrical components 98 can vary from application to application, as is known in the art, but are configured to perform various sensing or monitoring routines, as well as to store data related to operation of implantable IMD 40. In operation, the electronics module 92 is electrically connected to the capacitor assembly 64 and the energy source 94 such that, amongst other functions, the electronics module 92 causes the energy source 94 to charge and recharge the capacitor within capacitor assembly 64.

FIG. 3(a) shows capacitor assembly 64 prior to being placed within IMD 40. In one preferred embodiment, capacitor assembly 64 includes a pair of capacitors connected electrically in series by interconnections in electronics module 92. Capacitor assembly 64 is preferably a stacked capacitor configuration as described in greater detail below. Alternatively, capacitor assembly 64 can assume other forms known in the art such as a photoflash capacitor, a cylindrical capacitor, etc. Energy source 94, such as an electrochemical cell or battery, provides the electrical energy required to charge and re-charge capacitor assembly 64, and also powers electronics module 92.

Battery 94 is most preferably a high-capacity, high-rate, spirally-wound battery of the type disclosed in U.S. Pat. No. 5,439,760 to Howard et al. for "High Reliability Electrochemical Cell and Electrode Assembly Therefor" and U.S. Pat. No. 5,434,017 to Berkowitz et al. for "High Reliability Electrochemical Cell and Electrode Assembly Therefor," the disclosures of which are hereby incorporated by reference herein in their respective entireties.

Battery 94 may less preferably be a battery having spirally-wound, stacked plate or serpentine electrodes of the types disclosed, for example, in U.S. Pat. Nos. 5,312,458 and 5,250,373 to Muffoletto et al. for "Internal Electrode and Assembly Method for Electrochemical Cells;" U.S. Pat. No. 5,549,717 to Takeuchi et al. for "Method of making Prismatic Cell;" U.S. Pat. No. 4,964,877 to Kiester et al. for "Non-Aqueous Lithium Battery;" U.S. Pat. No. 5,147,737 to Post et al. for "Electrochemical Cell with Improved Efficiency Serpentine Electrode" and U.S. Pat. No. 5,468,569 to Pyszczek et al. for "Use of Standard Uniform Electrode Components in Cells of Either High or Low Surface Area Design," the disclosures of which are hereby incorporated by reference herein in their respective entireties. High-rate hybrid cathode cells are particularly suitable for use in conjunction with the present invention. In a preferred embodiment, a transverse shape and size of housing 90 depends solely upon the shape and size of electronics module 92 and capacitor assembly 64.

By preferably forming battery 94 to be thin, it is now possible for a combined thickness or height of battery 94/electronics module 92 to not overly exceed, preferably approximate, a height or thickness of capacitor assembly 64. As will be apparent to one of ordinary skill in the art, a height or thickness of housing 90 must be sufficient to encompass both capacitor assembly 64 and the combination battery 94/electronics module 92. In the preferred embodiment, because capacitor assembly 64 and the combination battery 94/electronics module 92 have approximately the same height or thickness, the corresponding height or thickness of housing 90 results in little, if any, wasted space, such that an overall height, and therefore volume, of housing 90 is optimized.

Figure 4:
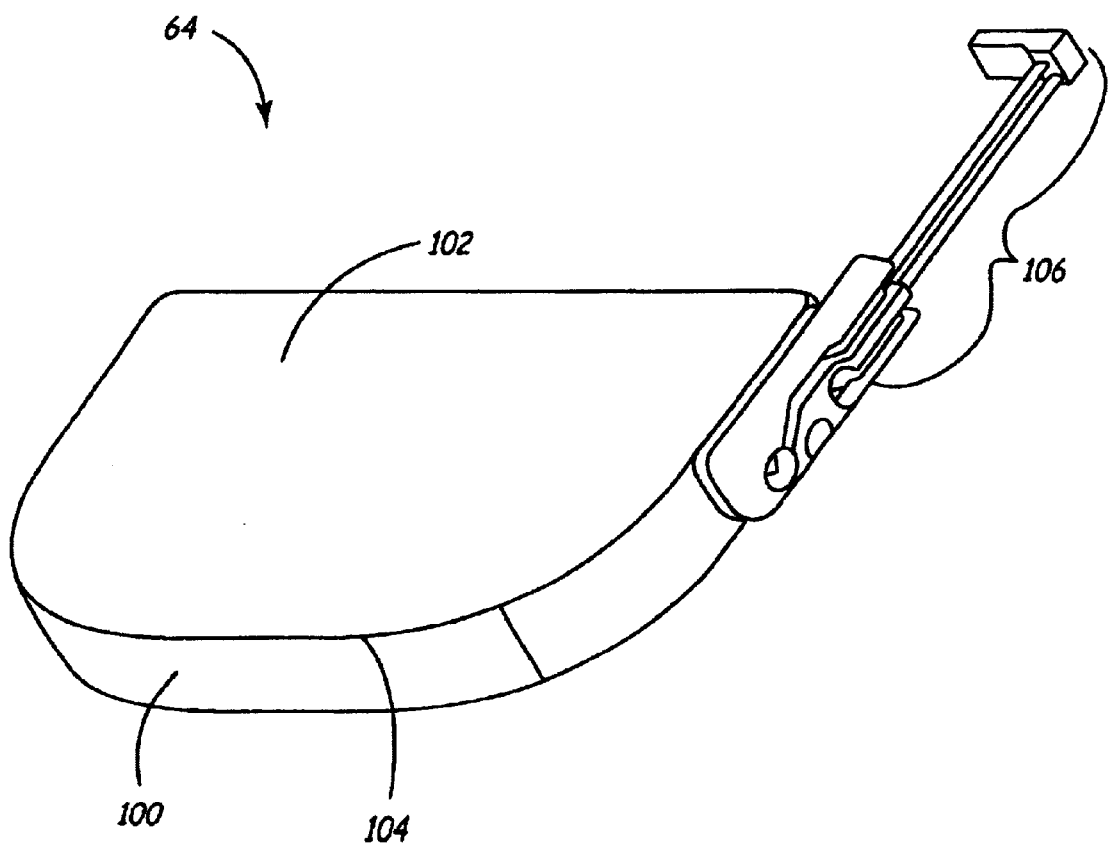
FIG. 4 shows a top perspective view of one embodiment of a capacitor assembly having a cover.

FIG. 4 shows a top view of one embodiment of capacitor assembly 64 (only one capacitor shown). Externally, capacitor assembly 64 comprises a case 100 and a cover 102 hermetically sealed along joint 104. A wiring harness assembly 106 is the means by which capacitor assembly 64 is electrically coupled to electronics module 92.

Figure 5:
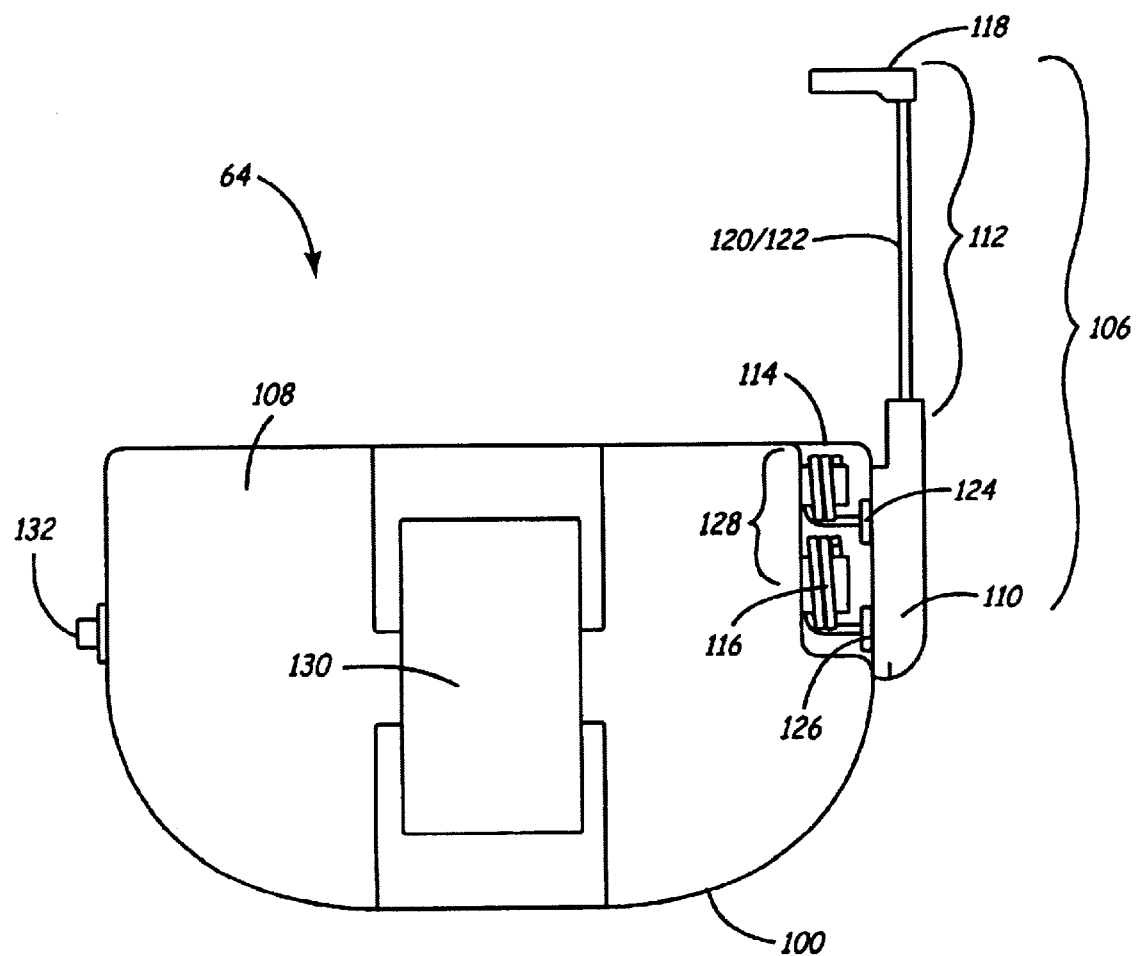
FIG. 5 shows a top view of the capacitor assembly of FIG. 4 having no cover.

FIG. 5 shows a top view of one embodiment of capacitor assembly 64 with cover 102 not present. Electrode stack assembly 108 is disposed within case 100. Wiring harness assembly 106 comprises connector block 110, wiring harness 112, anode feedthrough 114, cathode feedthrough 116, terminal connector 118. Wiring harness 112 comprises insulated leads 120 and 122. Terminal connector 118 is electrically coupled to electrode stack 108 via wiring harness 112, anode feedthrough 114 and cathode feedthrough 116. Capacitor assembly 64 is electrically coupled to electronics module 92 through terminal connector 118. Anode feedthrough 114 and cathode feedthrough 116 are inserted into case through wire guides 124 and 126. In one embodiment, a headspace portion of electrode stack assembly 108 (referred to herein as headspace 128) is insulated from case 100 and cover 102. The means of the present invention by which headspace insulation may be provided include molded, thermally-formed, die cut, or mechanically formed insulating materials and means, where the materials and means are stable in the environment of an electrolytic capacitor. Suitable materials from which headspace insulators may be formed include all those listed hereinabove respecting materials for forming wire guides 124 and 126. Another means of providing headspace insulation is to wrap electrically insulative tape, similar to wrapping tape 130, around headspace 128 to prevent the anode or cathode terminals from contacting case 100 or cover 102. Fill port ferrule 132 extends through case 100.

Figure 6:
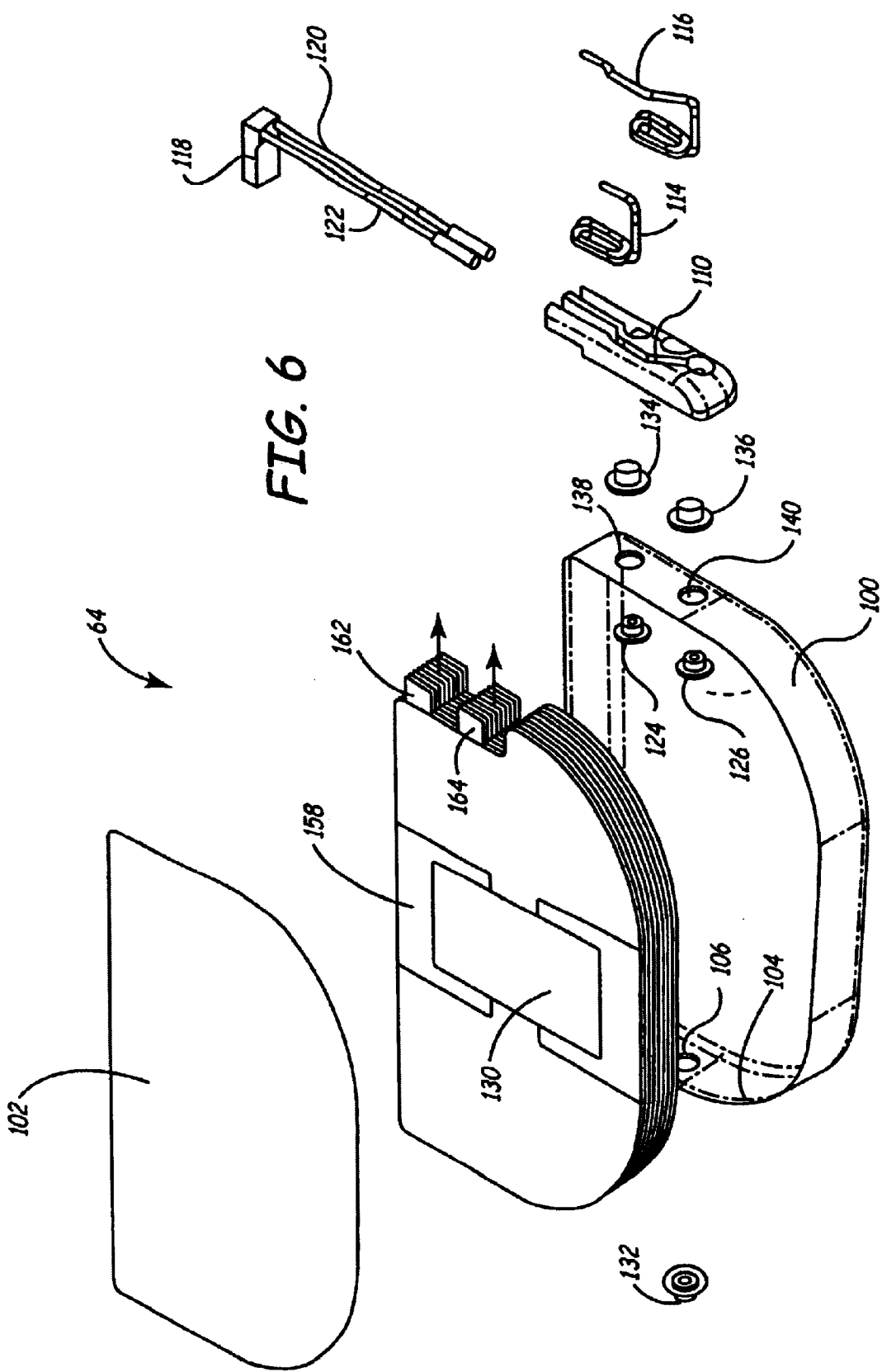
FIG. 6 shows an exploded top perspective view of the capacitor assembly of FIG. 5, wherein an insulative barrier is not shown.

FIG. 6 shows an exploded top perspective view of capacitor assembly 64 of FIG. 5 in a partially assembled state (with the insulative barrier not shown). Case 100, anode ferrule 134, cathode ferrule 136, and fill port ferrule 132 are first provided. Case 100 contains a means for accepting anode ferrule 134 therein, shown in FIG. 6 as anode feedthrough ferrule hole 138. Case 100 further contains a means for accepting cathode ferrule 136, shown in FIG. 6 as cathode feedthrough ferrule hole 140. Case 100 also includes a means for accepting fill port ferrule 132, shown in FIG. 6 as fill port hole 142. In a preferred embodiment, case 100 and cover 102 are formed of aluminum. In other embodiments, case 100 or cover 102 may be formed of any other suitable corrosion-resistant metal such as aluminum alloy, titanium or stainless steel, or may alternatively be formed of a suitable plastic, polymeric material or ceramic.

Case 100, cover 102 and capacitor assembly 64 of the present invention may additionally form a case negative capacitor (where case 100 and cover 102 are electrically connected to the cathode layers, and where case 100 and cover 102 are at the same electrical potential as the cathode layers, i.e., at negative potential), or a floating case capacitor (where case 100 and cover 102 are electrically connected neither to the cathode layers nor to the anode subassemblies, and where case 100 and cover 102 are at substantially no electrical potential or at an electrical potential that floats with respect to the respective potentials of the cathode layers and the anode sub-assemblies). In some embodiments, case 100 or cover 102 may be formed of an electrically non-conductive material or substantially electrically non-conductive material such as a suitable plastic, polymeric or ceramic material.

Ferrules 132, 134 and 136 are most preferably welded to case 100 (or otherwise attached thereto such as by a suitable epoxy, adhesive, solder, glue or the like). Radial flanges in anode ferrule 134 and cathode ferrule 136 provide a region for making a lap joint between the side wall of case 100 and around the perimeters of feedthrough ferrule holes 138 and 140.

In preferred methods of the present invention, a circumferential, laser weld is disposed in joint 104, and welding is carried out in two primary steps. First, a series of tack welds is made around the circumference of joint 104. The tack welds are most preferably made either by making adjoining, successive tack welds around the perimeter or by making a first tack weld at a first location along the perimeter, making a second weld diametrically opposed from the first weld along the perimeter, making a third weld adjacent to the first weld, making a fourth weld adjacent to the second weld, and so on. Finally, a final closing weld is made around the whole perimeter to hermetically seal tack welded joint 104.

Wire guides 124 and 126 most preferably contain annular, ramped, or "snap-in" features formed integrally therein. Those features prevent wire guides 124 and 126 from being pushed out of their respective ferrules during handling, but are most preferably formed such that insertion of wire guides 124 and 126 in their corresponding ferrules may occur using forces sufficiently low so as not to damage case 100 or ferrules 134 or 136 during the inserting step.

Wire guides 124 and 126 may be formed from any of a wide variety of electrically insulative materials that are stable in the environment of an electrolytic capacitor. In one preferred embodiment, the material from which wire guides 124 and 126 is made is an injection molded polysulfone. In other embodiments, wire guides 124 and 126 may be formed from other chemically resistant polymers such as fluoroplastics (e.g., ETFE, PTFE, ECTFE, PCTFE, FEP, PFA or PVDF), fluoroelastomers, polyesters, polyamides, polyethylenes, polypropylenes, polyacetals, polyetherketones, polyarylketones, polyether sulfones, polyphenyl sulfones, polysulfones, polyarylsulfones, polyetherimides, polyimides, poly(amide-imides), PVC, PVDC-PVC copolymers, CPVC, polyfurans, poly(phenylene sulfides), epoxy resins, silicone elastomers, nitrile rubbers, chloroprene polymers, chlorosulfonated rubbers, polysulfide rubbers, ethylene-polypropylene elastomers, butyl rubbers, polyacrylic rubbers, fiber-reinforced plastics, glass, ceramic and other suitable electrically insulative, chemically compatible materials.

As used in the specification and claims hereof, the foregoing acronyms have the following meanings: the acronym "ETFE" means poly(ethylene-co-tetrafluoroethylene); the acronym "PTFE" means polytetrafluoroethylene; the acronym "CTFE" means poly(ethylene-co-chlorotrifluoroethylene); the acronym "PCTFE" means polychlorotrifluoroethylene; the acronym "FEP" means fluorinated ethylene-propylene copolymer; the acronym "PFA" perfluoroalkoxy fluoropolymer; the acronym "PVDF" means polyvinylidene fluoride; the acronym "PVC" means polyvinyl chloride; the acronym "PVDC-PVC" means polyvinylidene chloride-polyvinyl chloride copolymer; and the acronym "CPVC" means chlorinated polyvinyl chloride.

Figure 7:
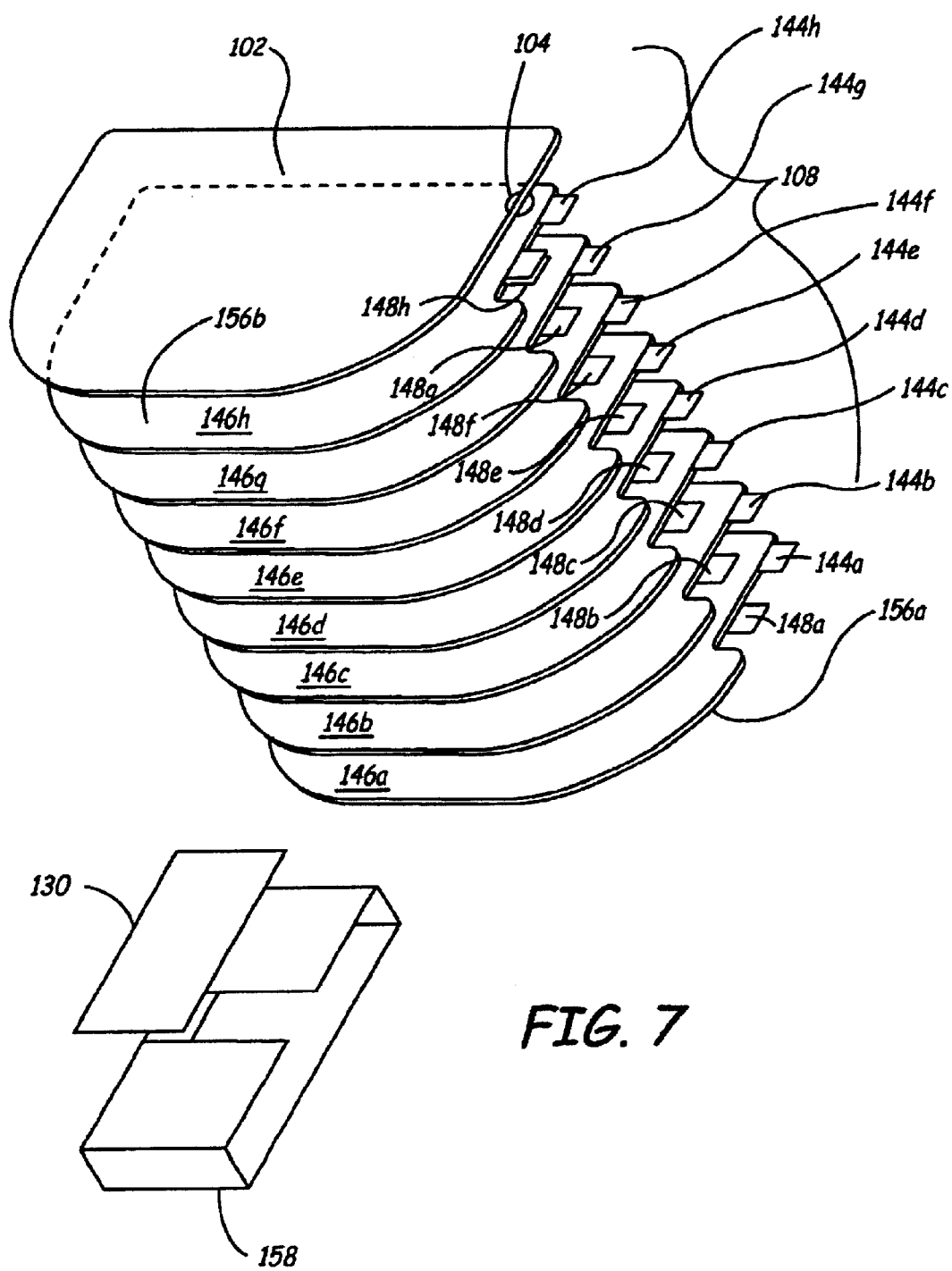
FIG. 7 shows an exploded top perspective view of one embodiment of an electrode stack of the capacitor assembly of FIG. 6.

FIG. 7 illustrates an exploded top perspective view of one embodiment of an electrode stack 108 of capacitor assembly 64. Electrode stack 108 most preferably comprises a plurality of anode/cathode subassemblies 146(a) through 146(h), outer separator layers 156a (top layer of anode/cathode subassembly 146(a)) and 156b (top layer of anode/cathode subassembly 146(h)), outer wrap 158 and wrapping tape 130. An anode tab 144 is coupled to each anode/cathode subassembly 146 as indicated by anode tabs 144(a) through 144(h) in FIG. 7. A cathode tab 148 is coupled to each anode/cathode subassembly 146 as indicated by cathode tabs 148(a) through 148(h) in FIG. 7.

Outer wrap 158 is most preferably die cut from separator material described infra, but may be formed from a wide range of other suitable materials such as polymeric materials, aluminum, suitable heat shrink materials, suitable rubberized materials and synthetic equivalents or derivatives thereof, and the like.

Wrapping tape 130 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on.

Outer wrap 158 and wrapping tape 130 together comprise an electrode stack wrap which has been discovered to help prevent undesired movement or shifting of electrode stack 108 during subsequent processing. It will now become apparent to one skilled in the art that many means other than those disclosed explicitly herein exist for immobilizing and securing electrode stack 108 during subsequent processing which accomplish substantially the same function as the electrode assembly wrap comprising outer wrap 158 and wrapping tape 130. Alternative means for immobilizing and securing electrode stack 108 other than those described hereinabove exist. Such alternative means include, but are not limited to, robotic or other mechanical clamping and securing means not necessarily forming a portion of electrode stack 108, adhesive electrolytes for forming separator layers 154, and so on.

It will be understood by those skilled in the art, that the precise number of anode/cathode subassemblies 146 selected for use will depend upon the energy density, volume, voltage, current, energy output and other requirements placed upon capacitor assembly 64. As few as two anode/cathode subassemblies 146 and as many as 50 anode/cathode subassemblies 146 are included.

Figure 8:
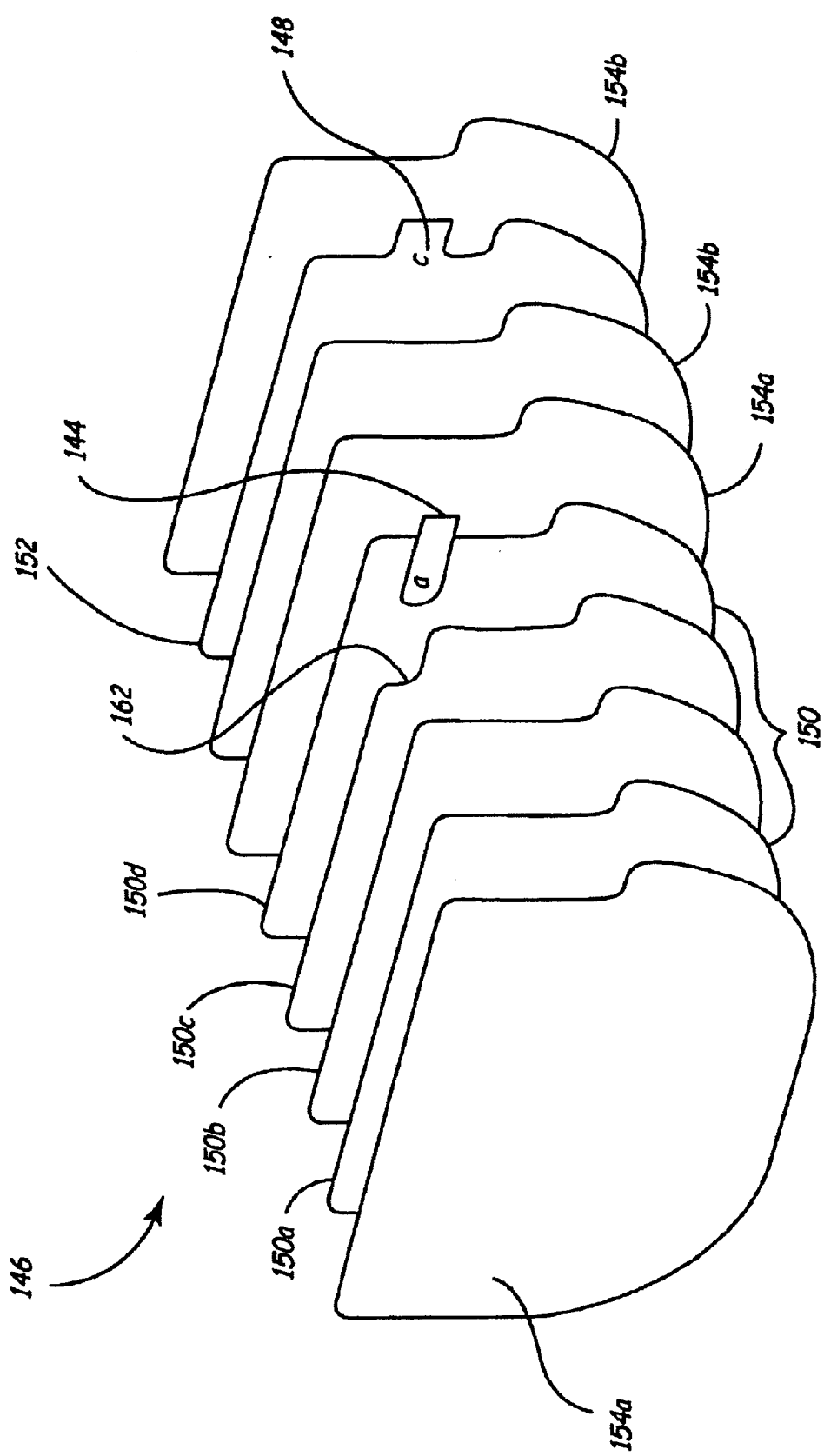
FIG. 8 shows an exploded view of one embodiment of a single anode/cathode subassembly of the capacitor of FIG. 7.

FIG. 8 shows an exploded view of one embodiment of a single anode/cathode subassembly 146. The capacitor design described herein employs a stacked configuration, where anode/cathode subassembly 146 comprises alternating substantially rectangularly-shaped anode layers 150 and cathode layers 152, with substantially rectangularly-shaped separator layers 154 being interposed therebetween. In one preferred embodiment, two individual separator layers 154(a) and 154(b) are disposed between anode layer 150 and cathode layer 152. One anode layer 150(a) has anode tab 144 attached thereto. Cathode layer 152 most preferably has cathode tab 148 formed integral thereto and projecting from the periphery thereof.

The shapes of anode layers 150, cathode layers 152 and separator layers 154 are primarily a matter of design choice, and are dictated largely by the shape or configuration of case 100 within which those layers are ultimately disposed. In a die apparatus according to one preferred method, the punch and cavity employed in forming those layers should be configured to produce layers having a desired predetermined shape, such as those shown in FIG. 8. A principal advantage of the capacitor construction is that anode layers 150, cathode layers 152 and separator layers 154 may assume any arbitrary shape to optimize packaging efficiency.

Anode layers 150, cathode layers 152 and separator layers 154 are most preferably formed of materials typically used in high quality aluminum electrolytic capacitors. Individual anode layers 150 are typically somewhat stiff and formed of high-purity aluminum processed by etching to achieve high capacitance per unit area. Cathode layers 152 are preferably high purity and are comparatively flexible. In one embodiment, separators 154 are made slightly larger than cathode layers 152 and anode layers 150 to ensure that a physical barrier is disposed between the anodes and the cathodes of finished capacitor assembly 64.

In one embodiment of capacitor assembly 64 of the present invention, and as shown in FIG. 8, anode/cathode subassembly 146 but one of a plurality of anode/cathode subassemblies 146(a) through 146(h) disposed within capacitor assembly 64. Likewise, a plurality of anode layers 150 and separator layers 154 are most preferably disposed within each sub-assembly, while a single cathode layer 152 is disposed within each anode/cathode subassembly 146. Anode/cathode subassembly 146 in FIG. 8 is but one embodiment, and is shown therein as most preferably comprising three unnotched anode layers 150(a) through 150(c), one notched anode layer 150(d) and one anode tab 144.

Similarly, it will be understood by those skilled in the art that the precise number of notched and unnotched anode layers 150, anode tabs 144, cathode layers 152 and separator layers 154 selected for use in a given embodiment of anode/cathode subassembly 146 will depend upon the energy density, volume, voltage, current, energy output and other requirements placed upon capacitor assembly 64.

It will now become apparent that a virtually unlimited number of combinations and permutations respecting the number of anode/cathode subassemblies 146, and the number of unnotched and notched anode layers 150, anode tabs 144, cathode layers 152 and separator layers 154 disposed within each anode/cathode subassembly 146, may be selected according to the particular requirements of capacitor assembly 146, and further that such combinations and permutations fall within the scope of the present invention.

Referring to FIG. 8 again, anode/cathode subassembly 146 most preferably comprises a plurality of non-notched anode layers 150(a) through 150(c), notched anode layer 150(d), anode tab 144 and anode tab notch 162. Anode layers 150(a) through 150(d) are formed of anode foil 164 (not shown in the Figures). It has been discovered that anode foil 164 is most preferably through-etched, has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, more preferably between about 75 and 150 micrometers, more preferably yet between about 90 and about 125 micrometers, and most preferably being about 100 micrometers thick, and a cleanliness of about 1.0 mg/m$^2$ respecting projected area maximum chloride contamination.

Thin anode foils are preferred, especially if they substantially maintain or increase specific capacitance while reducing the thickness of electrode stack 108, or maintain the thickness of electrode stack 108 while increasing overall capacitance. For example, it is contemplated that individual anode layers 150 have a thickness of about 10 micrometers, about 20 micrometers, about 30 micrometers, about 40 micrometers, about 50 micrometers, about 60 micrometers, about 70 micrometers, about 80 micrometers, about 90 micrometers, about 100 micrometers, about 110 micrometers, about 120 micrometers, about 130 micrometers, about 140 micrometers and about 150 micrometers.

In one preferred embodiment, anode foil 164 has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils for practicing the present invention are commercially available on a widespread basis.

Cathode layers 152 are most preferably formed from cathode foil 166 (not shown in the Figures). Some preferred parameters of cathode foil 166 have been discovered to include high surface area (i.e., highly etched cathode foil), high specific capacitance (preferably at least 200 microfarads/cm$^2$, and at least 250 microfarads/cm$^2$ when fresh), a thickness of about 30 micrometers, a cleanliness of about 1.0 mg/m$^2$ respecting projected area maximum chloride contamination, and a purity which may be less than corresponding to the starting foil material from which anode foil 65 is made.

In one preferred embodiment, cathode foil 166 has an initial purity of at least 99% aluminum, and more preferably yet of about 99.4% aluminum, a final thickness of about 30 micrometers, and an initial specific capacitance of about 250 microfarads per square centimeter.

In other embodiments, cathode foil 166 has a specific capacitance ranging between about 100 and about 500 microfarads/cm$^2$, about 200 and about 400 microfarads/cm$^2$, or about 250 and about 350 microfarads/cm$^2$, a thickness ranging between about 10 and about 150 micrometers, about 15 and about 100 micrometers, about 20 and about 50 micrometers, or about 25 and about 40 micrometers.

It is generally preferred that the specific capacitance of cathode foil 166 be as high as possible, and that cathode layer 152 be as thin as possible. For example, it is contemplated that individual cathode layers 152 have specific capacitances of about 100 microfarads/cm$^2$, about 200 microfarads/cm$^2$, about 300 microfarads/cm$^2$, about 400 microfarads/cm$^2$, about 500 microfarads/cm$^2$, about 600 microfarads/cm$^2$, about 700 microfarads/cm$^2$, about 800 microfarads/cm$^2$, about 900 microfarads/cm$^2$, or about 1,000 microfarads/cm$^2$. Suitable cathode foils 166 for practicing the present invention are commercially available on a widespread basis. In still other embodiments, cathode foil 166 is formed of materials or metals in addition to aluminum, aluminum alloys and "pure" aluminum.

Separator layers 154 are most preferably made from a roll or sheet of separator material 160. In one preferred embodiment, separator material 160 is a pure cellulose, very low halide or chloride content Kraft paper having a thickness of about 0.0005 inches, a density of about 1.06 grams/cm$^3$, a dielectric strength of 1,400 ac Volts per 0.001 inches thickness, and a low number of conducting paths (about 0.4/ft$^2$ or less). In one embodiment, separator layers 154 are cut slightly larger than anode layers 150 and cathode layers 152 to accommodate misalignment during the stacking of layers and to prevent subsequent shorting between electrodes of opposite polarity and case 100.

It is preferred that separator layers 154 be formed of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. Separator layers 154 may also be formed of materials other than Kraft paper, such as Manila paper, porous polymeric materials or fabric gauze materials. For example, porous polymeric materials may be disposed between anode and cathode layers of like those disclosed in U.S. Pat. Nos. 3,555,369 and 3,883,784 in some embodiments.

In a preferred embodiment, a liquid electrolyte saturates or wets separator layers 154 and is disposed within case 100. It is to be understood, however, that various embodiments of the present invention include within their scope a solid or adhesive electrolyte such as those disclosed in U.S. Pat. Nos., 5,628,801; 5,584,890; 4,942,501 and its continuations, U.S. Pat. Nos. 5,146,391 and 5,153,820. Note that in some embodiments of the present invention, an appropriate interelectrode adhesives/electrolyte layer may be employed in place of paper, gauze or porous polymeric materials to form separator layer 154.

It will also be understood by those skilled in the art that there exist many different types and methods for making anode foil 164, cathode foil 166 and separator material 160. What we disclose herein, therefore, are only preferred materials, methods and apparatus for making a preferred embodiment of capacitor assembly 64, and its various components, and not all the materials, methods and apparatus suitable for practicing the present invention and falling within the scope thereof.

The stacking process by which electrode stack 108 is most preferably made begins by placing outer wrap 158 into a stacking fixture followed by placing outer paper or separator layer 156*a* thereon. Next, cathode layer 152 is placed atop outer separator layer 156*a*, followed by separator layers 154*b* and 154*a* being disposed thereon. Cold-welded anode layer 150 is then placed atop separator layer 154*a*, followed by placing separator layers 154*b* and 154*a* thereon, and so on. The placement of alternating cathode layers 152 and anode layers 150 with separator layers 154*b* and 154*a* interposed therebetween continues in the stacking fixture until final cathode layer has been placed thereon.

In the embodiment of electrode stack 108 shown in FIG. 7, eight anode layers (anode layers 150(*a*) through 150(*h*)) and nine cathode layers (cathode layers 152(*a*) through 152(*i*)) are illustrated as comprising anode/cathode subassemblies 146(*a*) through 146(*h*). The voltage developed across each anode/cathode subassembly 146 (i.e., combined anode layer 150/separator layer 154/cathode layer 152) disposed within electrode stack 108 most preferably ranges between about 360 and about 390 Volts DC. As described below, the various anode layers of electrode stack 108 are typically coupled in parallel electrically, as are the various cathode layers of electrode stack 108.

It will now be understood by one skilled in the art that electrode stack 108 shown in FIG. 7 is merely illustrative, and does not limit the scope of the present invention in any way respecting the number or combination of anode layers 150, cathode layers 152, separator layers 154, anode tabs 144, cathode tabs 148, and so on. The number of electrode components is instead determined according to the total capacitance required, the total area of each layer, the specific capacitance of the foil employed and other factors.

In another embodiment of electrode stack 108, the number of anode layers 150 is varied in the stack. Such a design permits the fabrication of capacitors having the same layer area but nearly continuously varying different and selectable total capacitances that a user may determine by increasing or decreasing the number of anode layers 150 included in selected anode/cathode assemblies 146 (as opposed to adding or subtracting full anode/cathode layers 146 from electrode stack 108 to thereby change the total capacitance). Following placement of cathode layer 152(*i*) in electrode stack 108, outer layer 156*b* is placed thereon, and outer wrap 158 is folded over the top of electrode stack 108. Wrapping tape 130 is then holds outer wrap 158 in place and secures the various components of electrode stack 108 together.

The physical dimensions of separator layers 154 and outer separator layer 156 are conventionally somewhat larger than those of anode layers 150 and cathode layers 152 to prevent contact of the electrodes with the case wall or electrical shorting between opposing polarity electrode layers due to the presence of burrs, stray or particulate material, debris or imperfections occurring therein. The reliability and functionality of capacitor assembly 64 are compromised if a portion of anode layer 150 comes into contact with a conducting case wall, if a burr on the periphery of anode layer 150 or cathode layer 152 comes into contact with an adjoining layer of opposing polarity, or if separator layer 154 does not provide sufficient electrical insulation between adjoining opposite-polarity electrode layers and conducting particulate matter bridges the gap therebetween.

In one embodiment, additional separator material 160 disposed about the periphery of electrode stack 108 is referred to herein as separator overhang. Decreasing the amount of separator overhang increases the energy density of capacitor assembly 64. It is beneficial from an energy density optimization perspective, therefore, to decrease the amount or degree of separator overhang. The amount of separator overhang required has been discovered to be primarily a function of the stack-up tolerance characteristic of the stacking method employed. In known cylindrical capacitors, we discovered that the amount of separator overhang is typically on the order of 0.100 inches. Fayram et al. in the foregoing '851 patent describe a flat aluminum electrolytic capacitor wherein the housing of the capacitor has at least two internal alignment members. Those alignment members necessarily add volume to the capacitor while taking away from the total amount of "active" electrode material available, thereby also decreasing the energy density of the capacitor.

Figure 9:
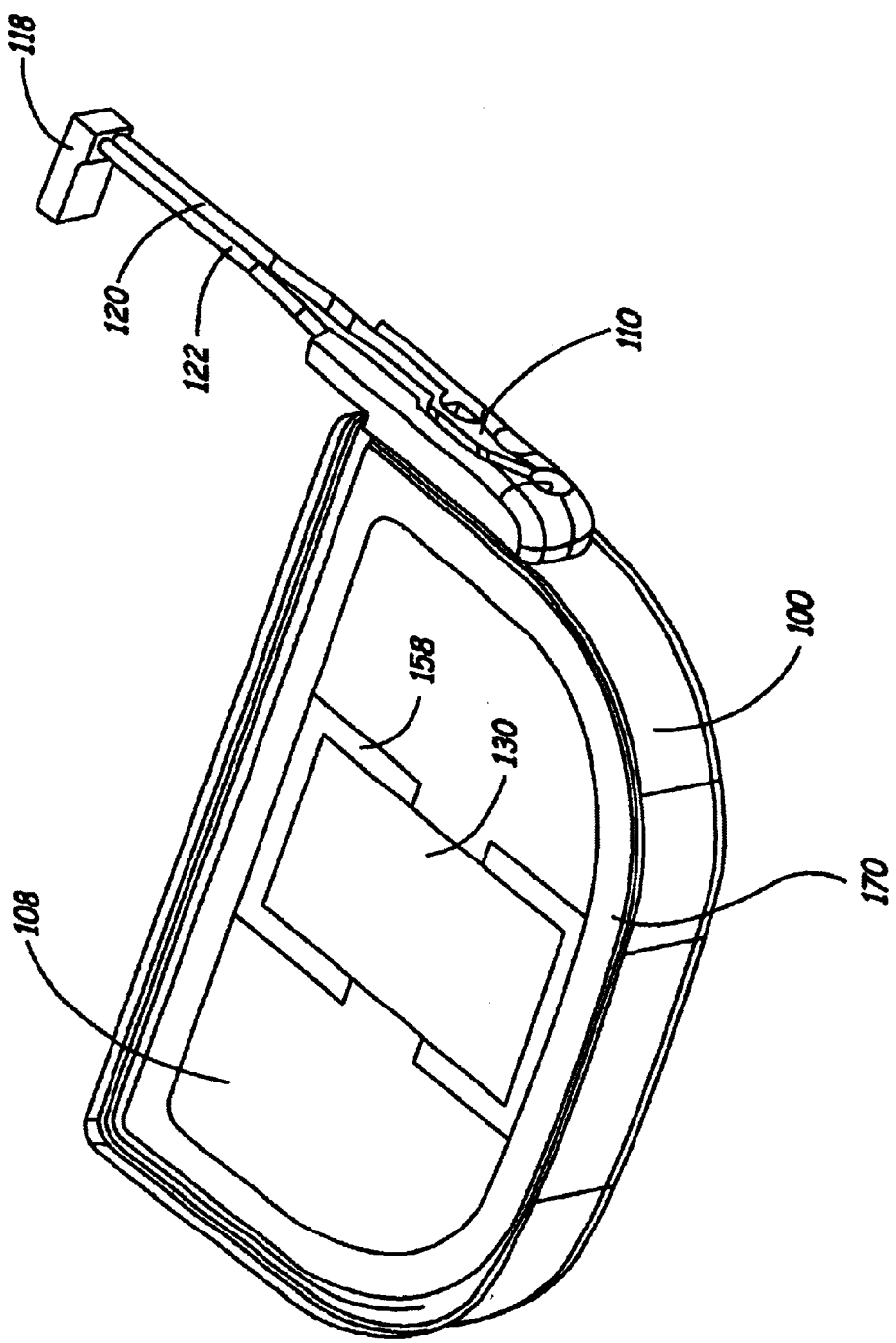
FIG. 9 shows a perspective view of a capacitor assembly having a liner of the present invention.

FIG. 9 represents one embodiment of the present invention wherein the implantable medical device includes capacitor assembly 64 having an insulative barrier positioned about electrode stack 108. In particular, the insulative barrier is located between electrode stack 108 and case 100. In one aspect, the insulative barrier is a liner 170 wherein the liner 170 closely surrounds electrode stack 108. Liner 170 encompasses electrode stack 108 within case 100 (shown with cover 102 removed). Outer wrap 158, secured by wrapping tape 130, wraps electrode stack 108 within liner 170. Wiring harness connector block 110 is coupled to electrode stack 108 through case 100.

Liner 170 is made of an appropriate thickness of material depending upon the mechanical design of electrode stack 108 (flat versus wound), the amount of separation layer overhang, separation between electrode stack 108 and case 100 walls, etc. In one embodiment liner 170 thickness is in the range of 0.001" to 0.10" and more preferably in the range of 0.003" to 0.005". Liner 170 thickness is also a function of the type of insulative material from which liner 170 is made. Additionally, if liner 170 is coated on case 100 or electrode stack 108, the liner 170 is less than 0.050 inches and more preferably less than, 0.001 inches, and more preferably less than 0.0005 inches.

Liner 170 is made of an electrically non-conductive material (i.e., insulative material). In one embodiment, liner 170 is made of a polymeric material or polymeric blend of materials, and in one preferred embodiment the polymeric material is polysulfone. Other suitable polymeric materials include polypropylene, polyethylene and ETFE. Optionally, liner 170 can be formed of other insulative materials, such as those materials previously disclosed herein for construction of wire guides 124 and 126. Liner 170 acts as a separator between the electrode stack 108 and case 100, and alternatively could be made porous or of porous materials, including having holes therethrough. Other suitable electrical non-conducting materials for liner 170 will become apparent to those skilled in the art after reading the present application.

Liner 170 mechanical design has numerous embodiments depending upon the electrode stack 108 configuration. In applications where the desired shape of capacitor assembly 64 has a low thickness to width aspect ratio, a stacked plate electrode 108 design is preferred to achieve optimal energy density. Liner 170 can be constructed of a single part, a two part assembly, or optionally made with multiple component construction. Various embodiments of liner 170 mechanical design are described in detail later in this specification. The use of liner 170 extends to cylindrical or other capacitor assembly 64 shapes. Although line r170 is thermoformed or molded in one embodiment, in another preferred embodiment liner 170 is coated or deposited on the inside of case 100 or electrode stack 108.

Figure 10:
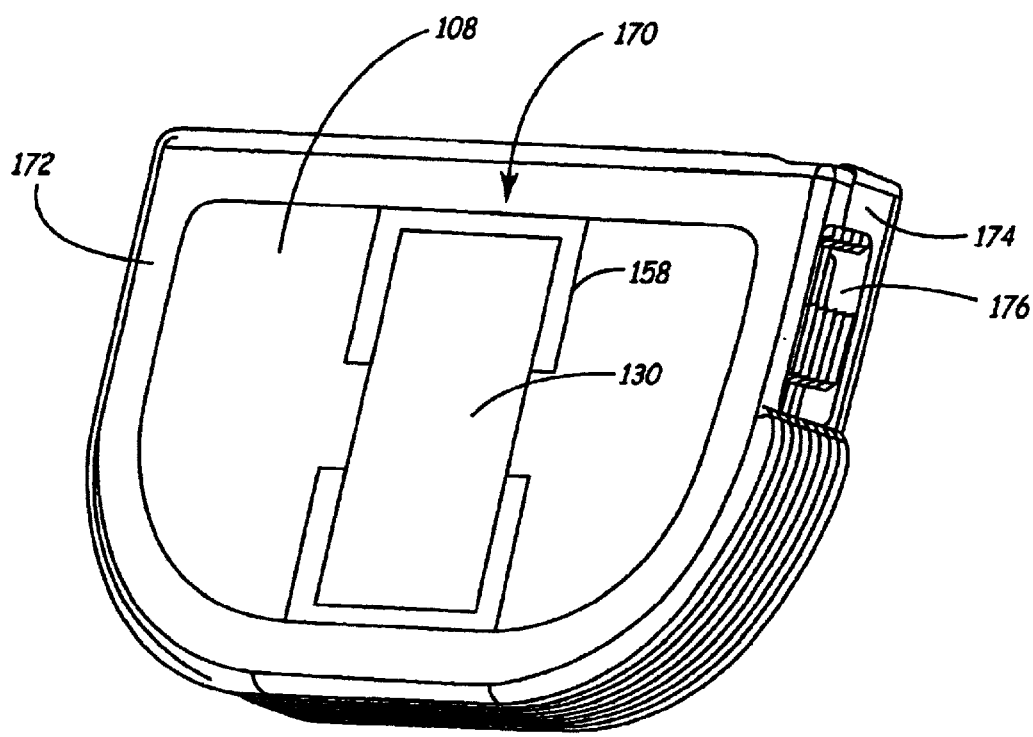
FIG. 10 shows a perspective view of the capacitor assembly and the orientation of the anode/cathode assemblies at the liner.

FIG. 10 illustrates liner 170 encompassing electrode stack 108 in cutaway view outside of case 100 with wiring harness assembly 106 removed. In one embodiment, liner 170 is constructed in two parts as shown. Liner 170 consists of a first part 172 and a second part 174. Electrode stack 108 is positioned between first part 172 and second part 174. Anode feedthrough 114 positioned within wire guide 124 inside anode ferrule 134, and cathode feedthrough 116 positioned within wire guide 126 inside cathode ferrule 136, extend through a headspace aperture 176 in liner 170. Similarly, fill port ferrule extends through fill port aperture 178 through liner 170.

Figure 11A:
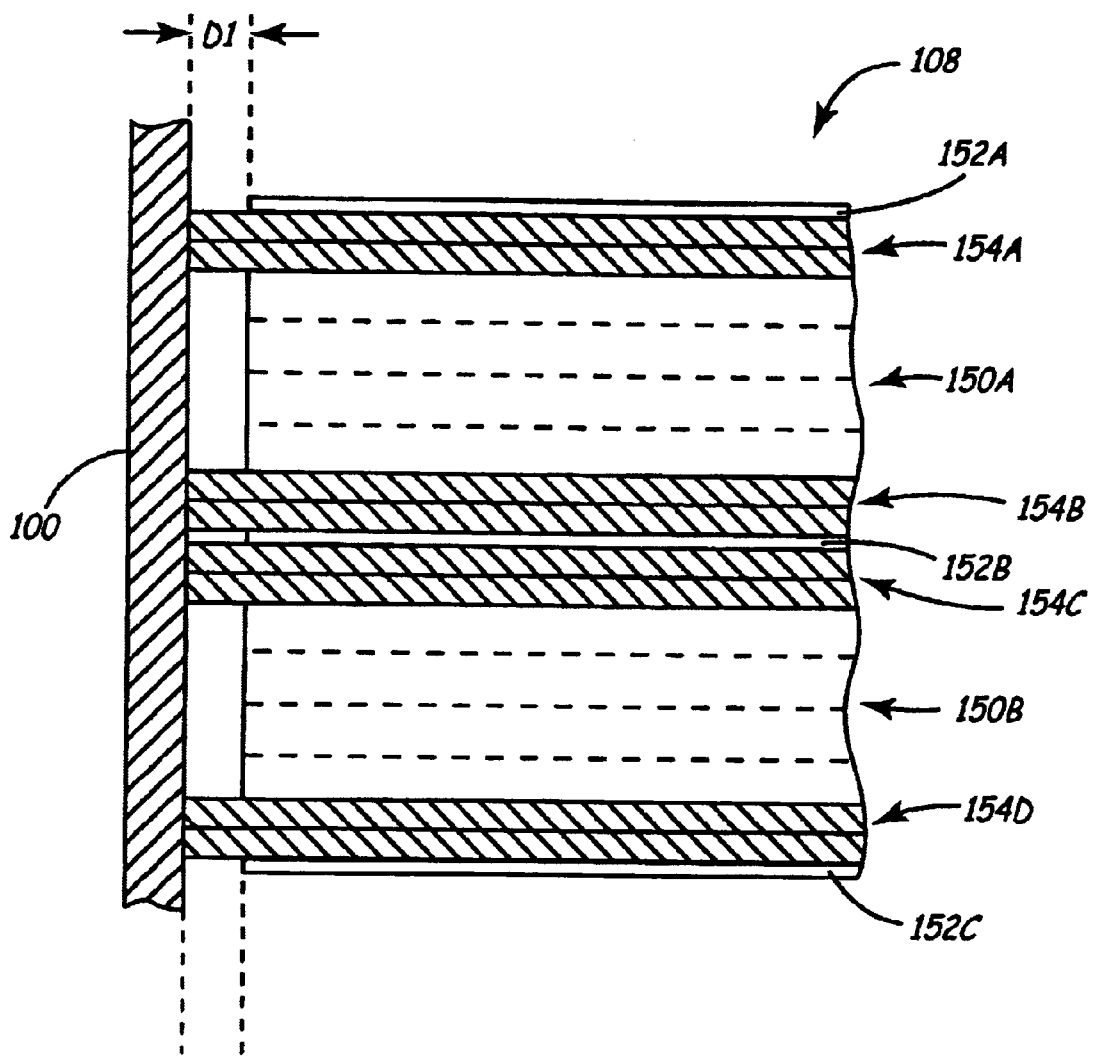
FIG. 11(a) is a partial cross-sectional view of a capacitor assembly for use with an implantable medical device.

FIG. 11(a) is a partial cross-sectional edge view of the relative positions of a prior art capacitor assembly 64, electrode stack 108, and anode/cathode subassemblies 146 with respect to case 100 (without insulative barrier or liner 170). For clarity, in the following paragraphs, each anode/cathode subassembly is referred to as an anode "layer," cathode "layer" and separator "layer," even though each "layer" may be of a multilayer or multiplate construction as previously detailed herein. Separator layers 154A, 154B, 154C, 154D overhang corresponding anode layers 150A, 150B and cathode layers 152A, 152B, 152C. The separator layer 154A, 154B, 154C, 154D overhang is approximately 0.100 inches, represented by distance "D1". Sufficient separator overhang must be maintained for proper clearance between the outside edges of anode layers 150A, 150B, case 100 and the corresponding cathode layers 152A, 152B, 152C. As shown, the surface area (and corresponding energy density potential) of capacitor layers 152A, 152B, 152C, and anode layers 150A, 150B are minimized by the amount of separator overhang D1.

Figure 11B:
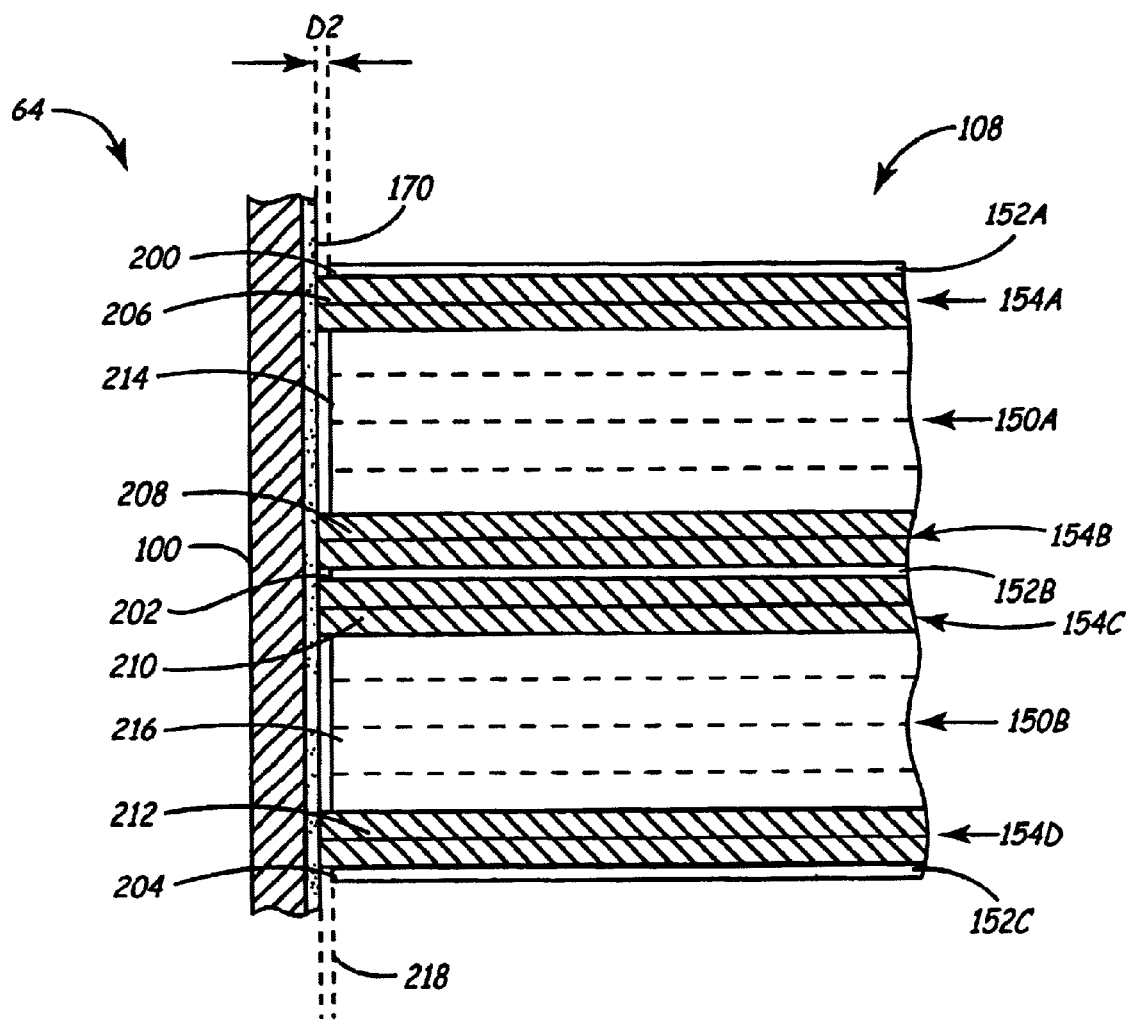
FIGS. 11(b) through 11(d) are partial cross-sectional views showing an end view of the position of anode/cathode subassemblies/layers of the capacitor assembly with respect to the case and liner.

In FIG. 11(b), a partial cross-sectional edge view is shown illustrating one exemplary embodiment of capacitor assembly 64 having liner 170 disposed between electrode stack 108 and case 100, according to the present invention. In particular, first cathode layer 152A includes a cathode layer outer edge 200, second cathode layer 152B includes a cathode layer outer edge 202, and third cathode layer 152C includes a cathode layer outer edge 204; separator layer 154A includes outer edge 206, separator layer 154B includes outer edge 208, separator layer 154C includes outer edge 210 and paper layer 154D includes outer edge 212; and anode layer 150A includes an outer edge 214 and anode layer 150B includes an outer edge 216. Thus, liner 170 is disposed between case 100 and the outer edges 200, 202, 204 of corresponding cathode layers 152A, 152B, 152C, the outer edges 214, 216 of corresponding anode layers 150A, 150B, and the outer edges 206, 208, 210, 212 of corresponding separator layers 154A, 154B, 154C, 154D.

Due to the presence of insulative liner 170, separator layers 154A, 154B, 154C, 154D only need to extend a minimum distance D2 beyond the outer edges 214, 216 of anode layers 150A, 150B while maintaining electrical or mechanical isolation of those layers from the case. Preferably, separator layers 154A, 154B, 154C, 154D extend a minimum distance D2 beyond outer edges 214, 216 and contact the liner 170. Preferably, distance D2 ranges from 0.050 inches to 0.100 inches, and more preferably ranges from 0.005 inches to 0.050 inches, and in one preferred embodiment is 0.005 inches. By minimizing the separator layer overhang distance D2, the surface area of cathode layers 152A, 152C and anode layers 150A, 150B are maximized. In the exemplary embodiment shown, the outer edges 200, 202, 204 of corresponding cathode layers 152A, 152B, 152C are substantially aligned with the outer edges 214, 216 of corresponding anode layers 150A, 150B, represented by dashed line 218. Alternatively, the separator layer overhang is greater than distance D2 and allowed to "curl" or wrap around.

Figure 11C:
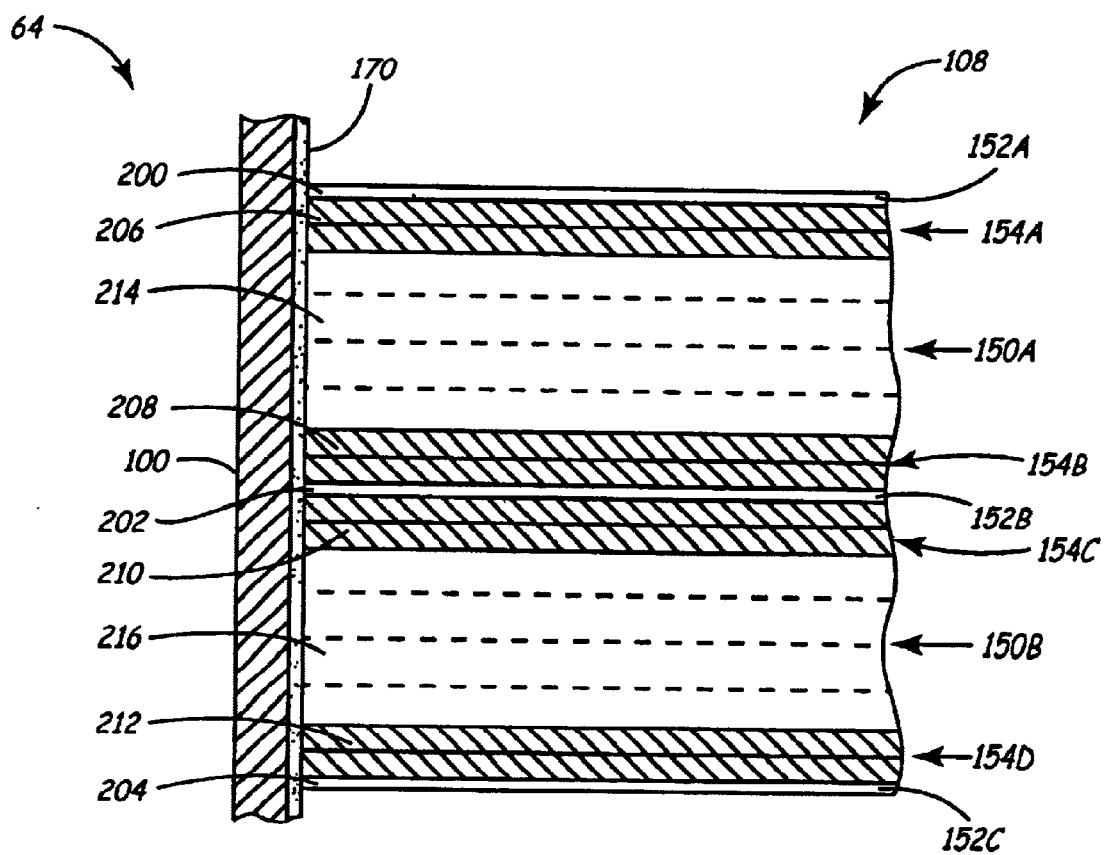

In FIG. 11(c), a partial cross-sectional edge view of capacitor assembly 64 is shown illustrating another exemplary embodiment of the present invention. The use of liner 170 disposed between case 100 and electrode stack 108 allows for separator layer overhang to be eliminated. Cathode layer outer edges 200, 202, 204 and anode layer outer edges 214, 216 are substantially aligned with separation layer outer edges 206, 208, 210, 212. These outer edges extend to liner 170, positioned immediately adjacent case 100, thereby maximizing the size of electrode stack 108.

Figure 11D:
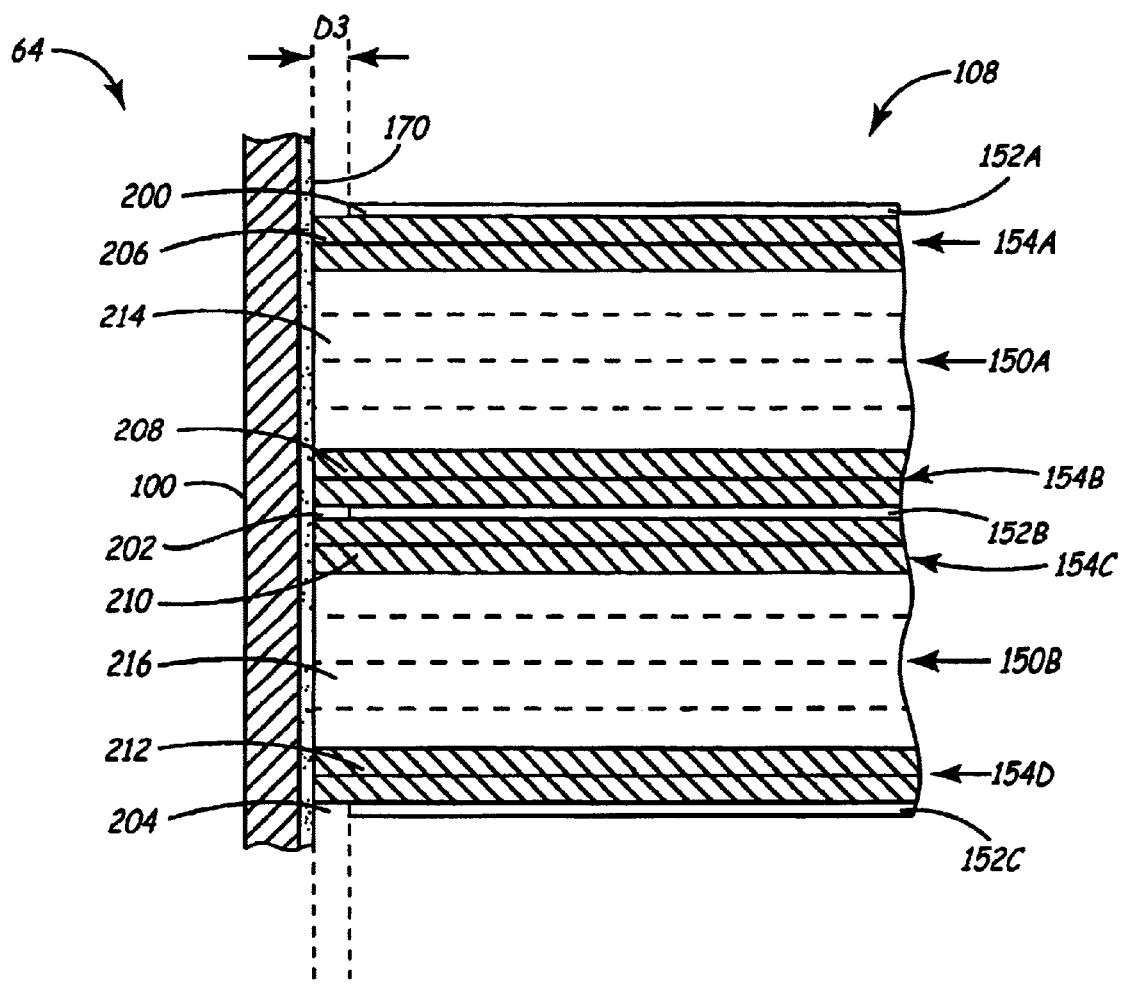

In FIG. 11(d), a partial cross-sectional edge view is shown illustrating yet another embodiment of the present invention. Insulative liner 170 is immediately adjacent case 100, and no separator overhang exists. In particular, the separator layer outer edges 206, 208, 210, 212 and the anode layer outer edges 214, 216 extend beyond the cathode layer outer edges 200, 202, 204, and more preferably, extend to insulative liner 170. In one exemplary embodiment, separator layer outer edges 206, 208, 210, 212 and anode layer outer edges 214, 216 are in substantial alignment. Cathode layer outer edges 200, 202, 204 are recessed a distance D3 from the separator layer and anode layer outer edges. Preferably, distance D3 ranges from 0.050 inches to 0.100 inches more preferably from 0.005 inches to 0.050 inches, allowing for maximization of the size of electrode stack 108. It may be desirable to maintain recessed distance D3 between the cathode layer outside edges 200, 202, 204 and the anode layer outside edges 214, 216 in order to eliminate chances of electrical contact and/or arcing between these layers.

Figure 12:
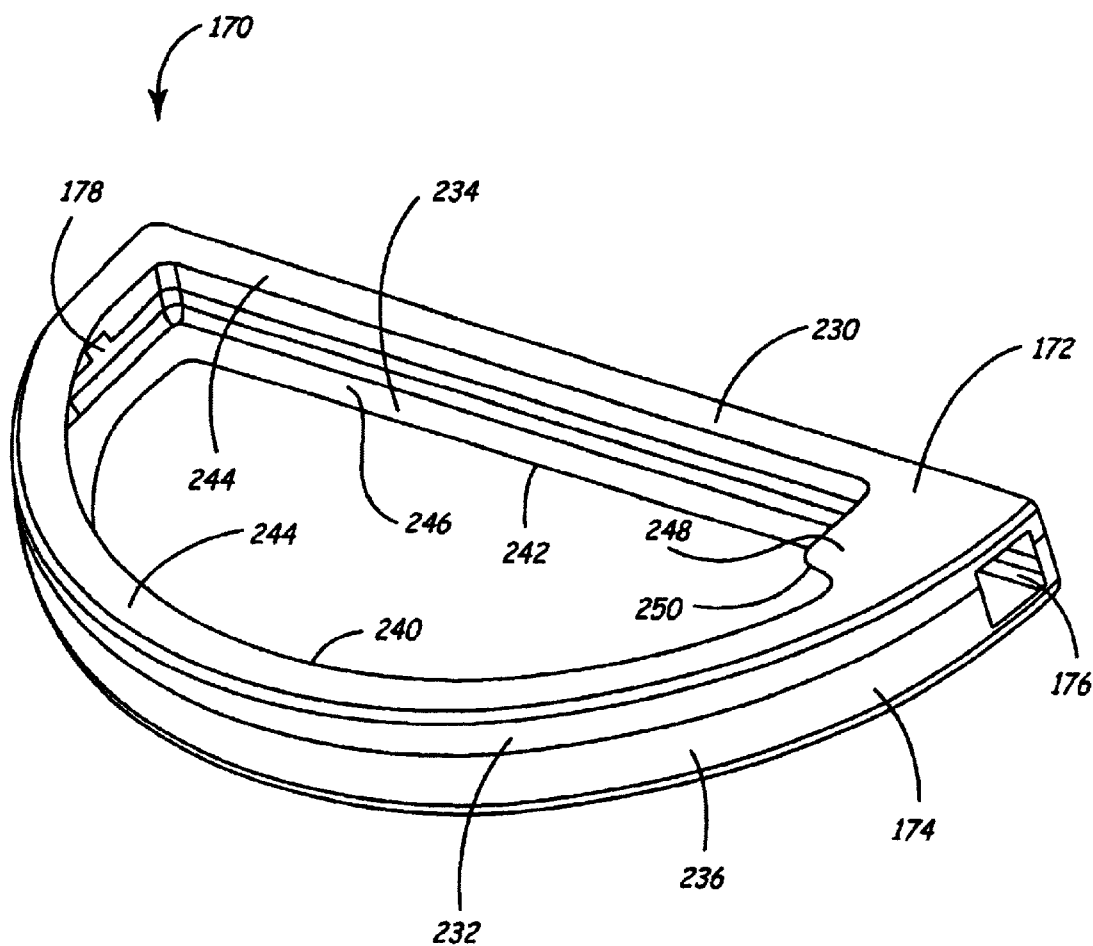
FIG. 12 shows a perspective view of one exemplary embodiment of a capacitor case liner of the present invention.

FIG. 12 illustrates one preferred embodiment of liner 170. Liner 170 is a two part assembly, including first part 172 and second part 174. First part 172 includes first planar member 230 and first outer edgewall 232. First outer edgewall 232 extends substantially perpendicular from first planar member 230. In one preferred embodiment, first outer edgewall 232 extends about the outer perimeter of first planar member 230. Similarly, second part 174 includes second planar member 234 and second outer edgewall 236. Second outer edgewall 236 extends substantially perpendicular from second planar member 234. In one preferred embodiment, second outer edgewall 236 extends about the outer perimeter of second planar member 234.

After liner 170 and electrode stack 108 are placed into case 100 and joint 104 sealed between case 100 and cover 102, capacitor assembly 64 is filled with electrolyte. Since the filled capacitor assembly 64 thickness is generally highest at the center, it is beneficial to remove material in the center of liner 170, forming a first cutout region 240 in first planar member 230 and a second cutout region 242 in second planar member 234. As such, first cutout region 240 and second cutout region 242 aid in keeping capacitor assembly 64 thickness to a minimum. Cutout region 240 is made such that lips 244, 246 remain to fixedly retain the top and bottom of electrode stack 108 (not shown in FIG. 12). Additionally, lips 244, 246 are beneficial in keeping the separator layer from finding its way into joint 104 where it could cause a failed or low quality weld or crimp. Alternatively, the widths of lips 244, 246 are minimized, or removed, such that they do not overhang electrode stack 108 to further minimize the total thickness of capacitor assembly 64. Reduction/removal of lips 244, 246 is balanced with the desire to keep separator layer 154 and separator layer 156 out of the area of joint 104.

Additional features provided by liner 170 are flaps 248, 250 to insulate headspace 128 from case 100 and cover 102. In one embodiment, an insulative barrier (formed from the same or different material as that used to form liner 170) is disposed between flaps 248, 250 to provide insulation between the anode tab 144 and cathode tab 148. Preferably, first part 172 and second part 174 are formed using a molding process. Other liner 170 features provide improved manufacturability for electrode stack 108 insertion into case 100 and reduction in the number of components handled.

Figure 13:
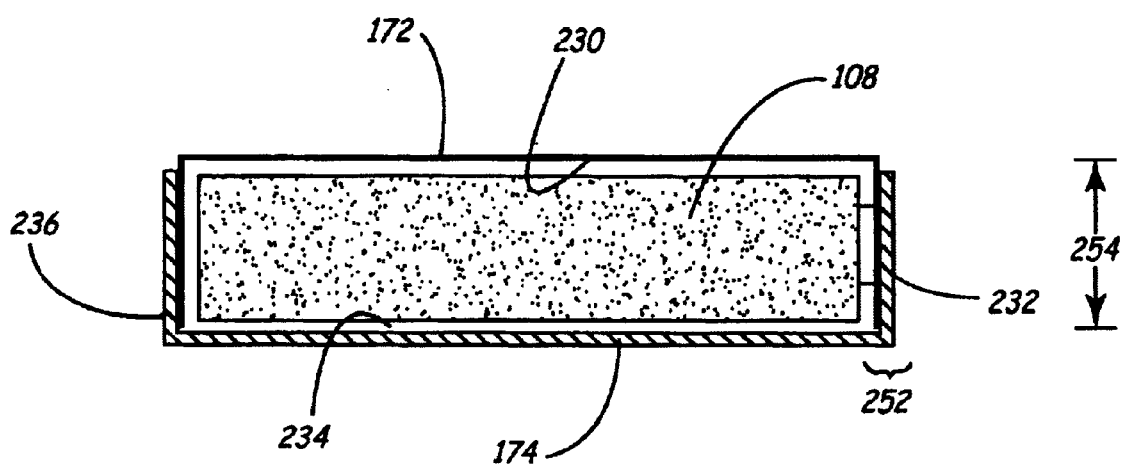
FIG. 13 shows a cross-sectional view of a liner around an electrode stack.

FIG. 13 shows an end view of liner 170 positioned around electrode stack 108. In one preferred embodiment, liner 170 consists of first part 172 and a second part 174. Electrode stack 108 is positioned between first part 172 and second part 174 such that second outer edgewall 236 overlaps first outer edgewall 232 to form an outer edge assembly 252 having an overlapping region 254. First outer edgewall 232 alternatively overlaps second outer edgewall 236 in other orientations. Outer edge assembly 252 operates to assure isolation of the outer edge of electrode stack 108 from case 100.

Figure 14:
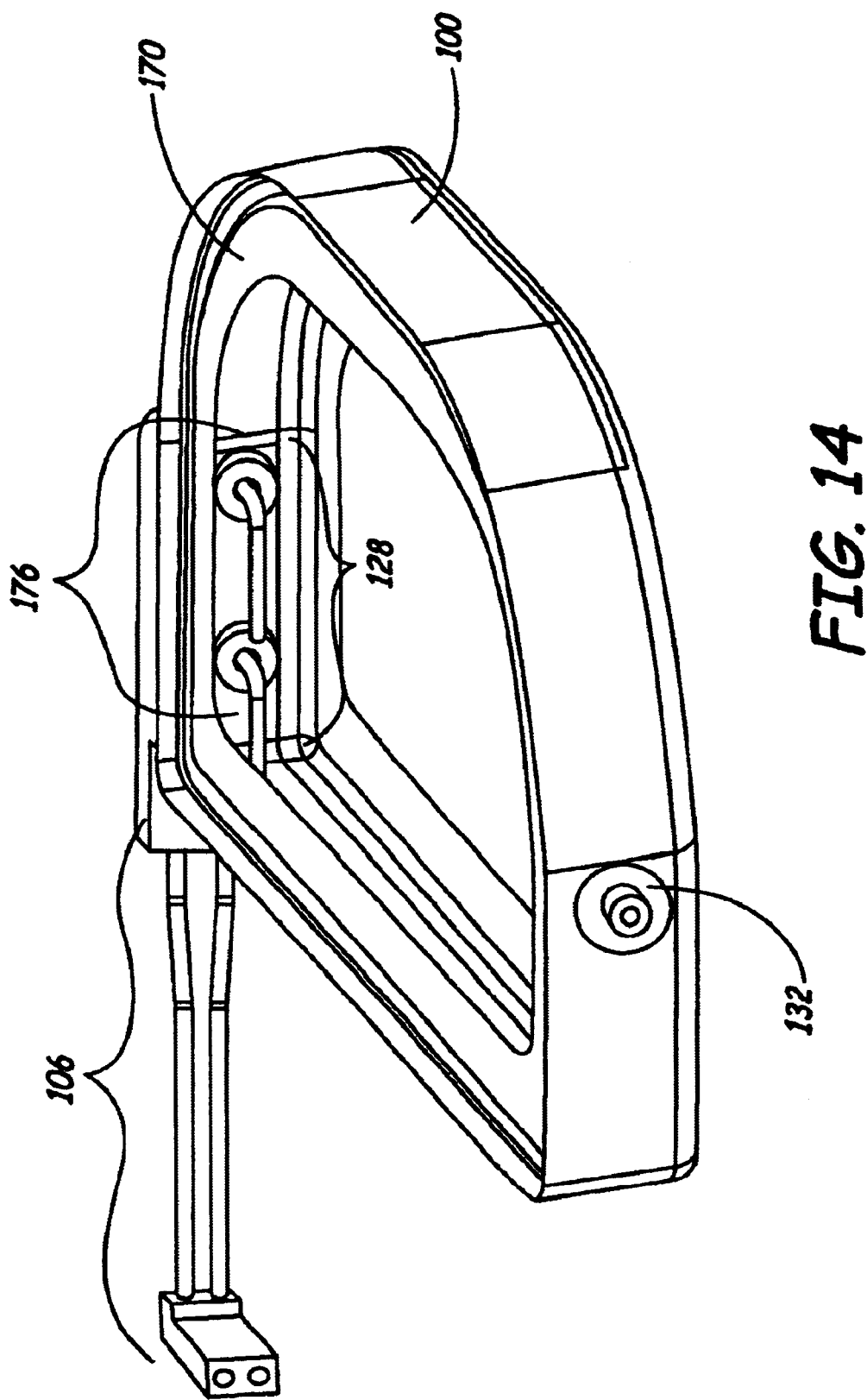
FIG. 14 shows a perspective view of one exemplary embodiment of a capacitor assembly liner according to the present invention.

FIG. 14 shows an alternate view of liner 170, wherein liner 170 is inserted in case 100 with electrode stack 108 removed. Wiring harness assembly 106 is shown installed such that the characteristics and orientation of headspace aperture 176 in liner 170 with respect to headspace 128 are apparent. For clarity, flaps 248 and 250 are not shown.

Figure 15:
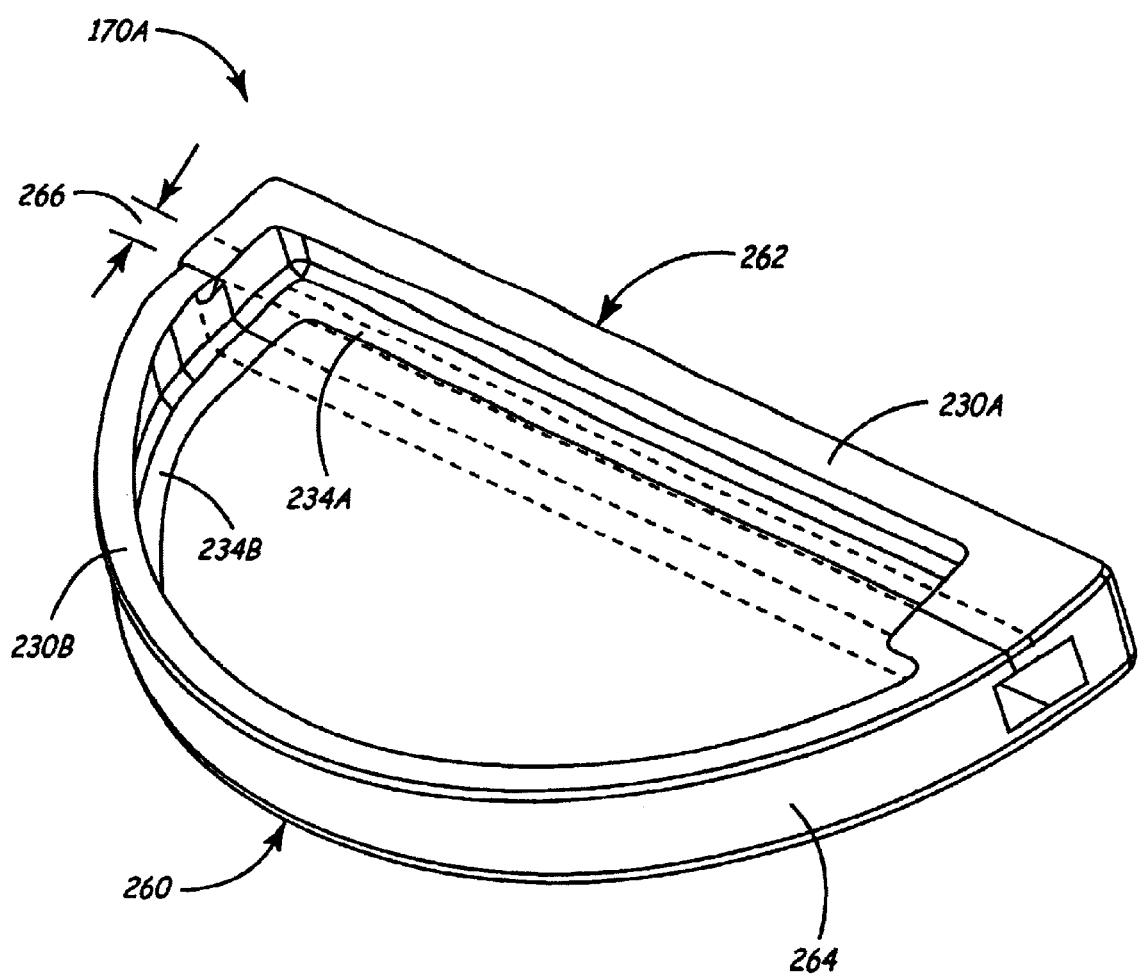
FIG. 15 shows a perspective view another embodiment of a capacitor assembly liner with an alternative overlapping structure.

FIGS. 15 through 18 illustrate alternative embodiments of liner 170 providing additional flexibility in capacitor assembly 64 design. Liner 170 alternatively separates into two (or more) parts along one of any of the three dimensions. As such, in the following paragraphs liner 170 is described relative to the position shown in the figures. In FIG. 15, liner 170 has a two part construction, including a front part 260 and a back part 262. Liner 170A includes planar members 230A, 230B, second planar members 234A, 234B and sidewall 264. When in a closed or operational position, overlapping region 266 of front part 260 and back part 262 extends through first planar members 230A, 230B, second planar members 234A, 234B, and sidewall 264.

Figure 16:
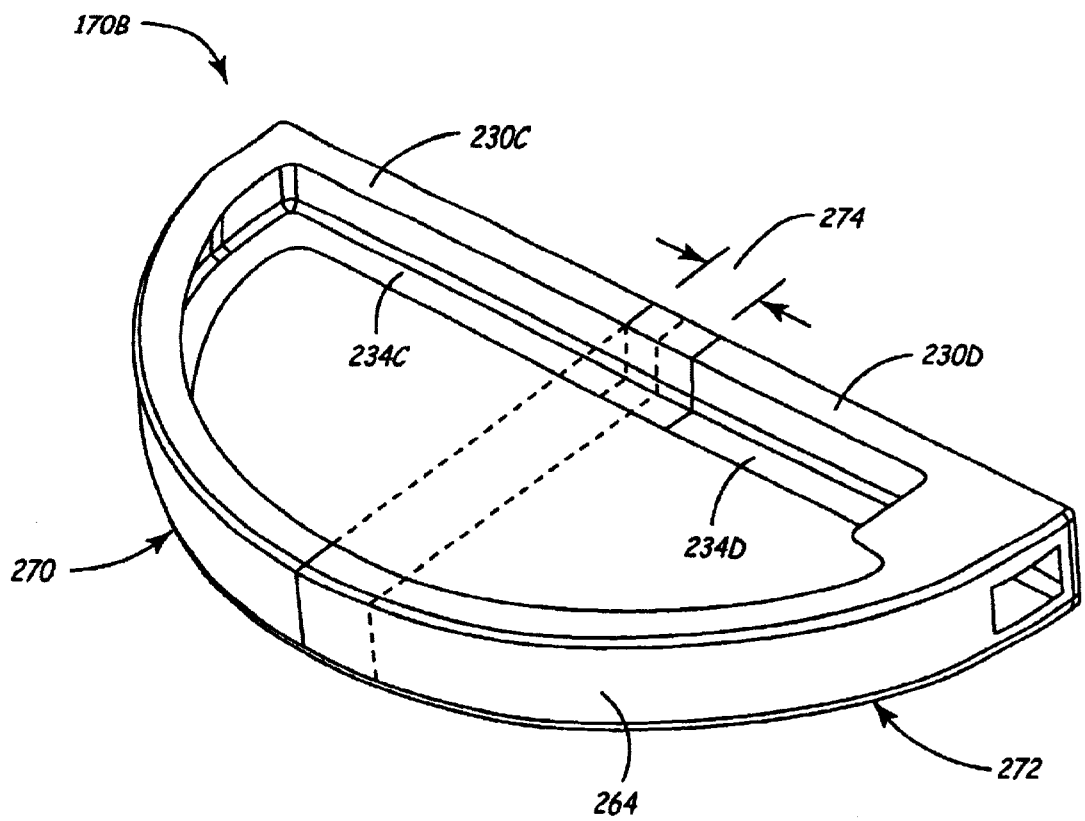
FIG. 16 shows a perspective view another embodiment of a capacity assembly liner illustrating an overlapping structure.

In FIG. 16, an alternative embodiment of liner 170 is shown at 170B. Liner 170B has a two part construction, including a first side part 270 and a second side part 272. Liner 170B includes first planar members 230C, 230D, second planar members 234C, 234D and sidewall 264. When in a closed or operational position, overlapping region 274 of first side part 270 and second side part 272 extends through first planar members 230C, 230D, second planar members 234C, 234D, and sidewall 264.

Figure 17:
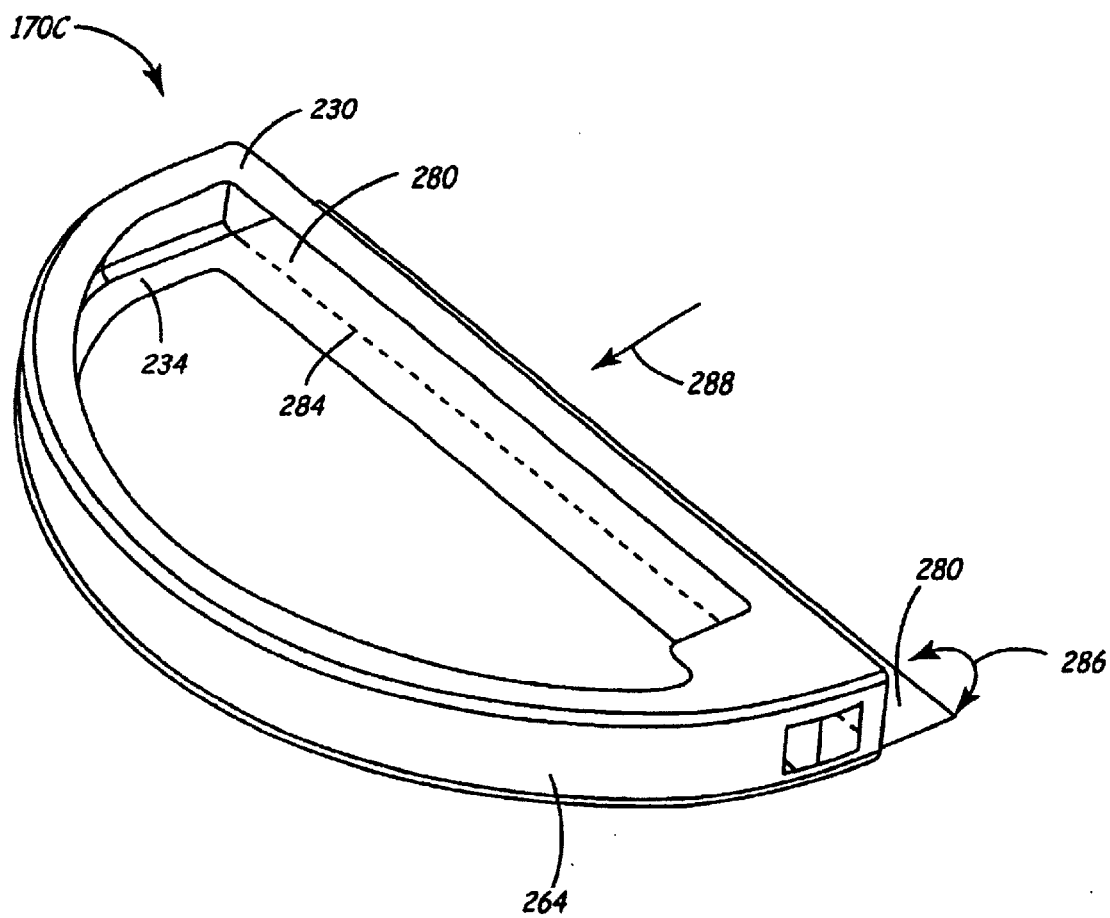
FIG. 17 shows a perspective view of another embodiment of a capacitor assembly liner having a hinged lid.

In FIG. 17, another alternative embodiment of liner 170 according to the present invention is shown at 170C. Liner 170C includes backwall 280 which is part of sidewall 264. Backwall 280 operates as part of a hinged door assembly 282. In particular, backwall 280 is hingedly secured to second planar member 234 by a hinge mechanism, indicated by dashed line 284. Hinged mechanism 284 may comprise a separate mechanical mechanism or, more preferably, comprises a weakened interface between backwall 280 and second planar member 234. Hinged door assembly 282 allows backwall 280 to be moved between an open position shown and a closed position, indicated by arrow 286. Hinged door assembly 282 allows for electrode stack 108 to be inserted within liner 170C, indicated by directional arrow 288.

FIGS. 18A through 18D illustrate another exemplary embodiment of the liner in accordance with the present invention, indicated at 170D, in which liner 170D is of a single, unitary piece design. In particular, liner 170D is a single unitary member having a "lamshell" design which allows it to be movable between an open position and a closed position. Liner 170D is shown in a closed position. Liner 170D includes backwall 280 having a first hinge mechanism 284A and a second hinge mechanism 284B which can be similar to the hinge mechanism 284 previously described herein. Liner 170D may also include a fill port mechanism 300 extending therethrough.

Figure 18B:
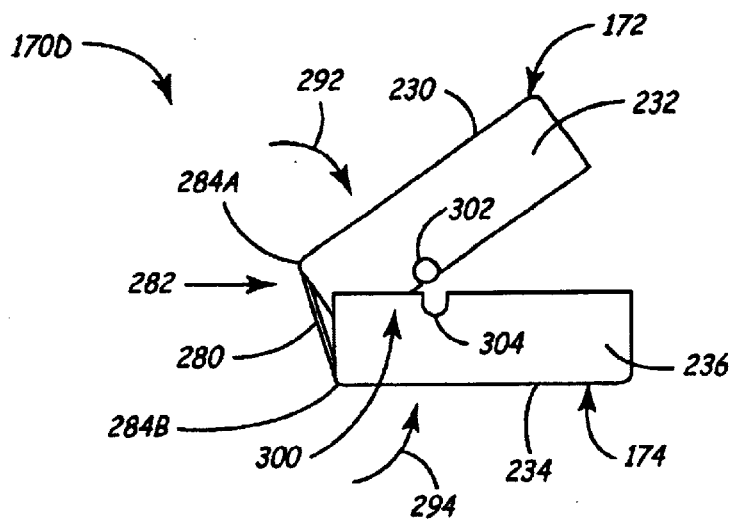
FIGS. 18(a) through 18(d) are perspective views illustrating another embodiment of a capacitor assembly liner having a one-piece construction.

Referring also to FIG. 18B, liner 170D is shown in a partially open position. First part 172 is moveable relative to second part 174 via first hinged mechanism 284A and second hinged mechanism 284B, indicated by arrows 292, 294. In the exemplary embodiment shown, locking mechanism 300 includes a fill mechanism 302 in first outer edge wall 232 and a notch 304 in second outer edge wall 236. The notch 304 is sized for securely receiving or snap fit of fill mechanism 302. The fill mechanism 302 is in operational alignment with the notch 304.

Figures 18C, 18D:
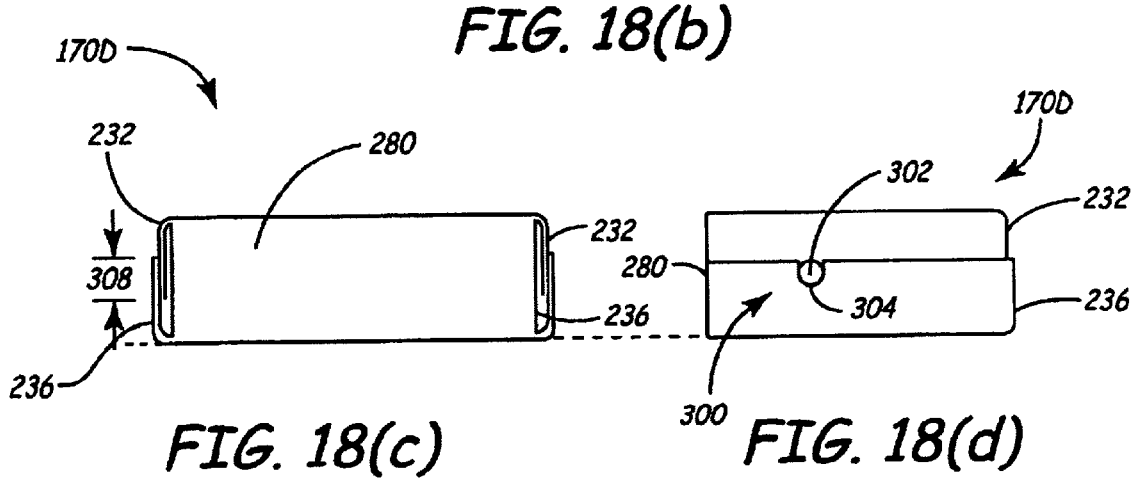
Figure 18A:
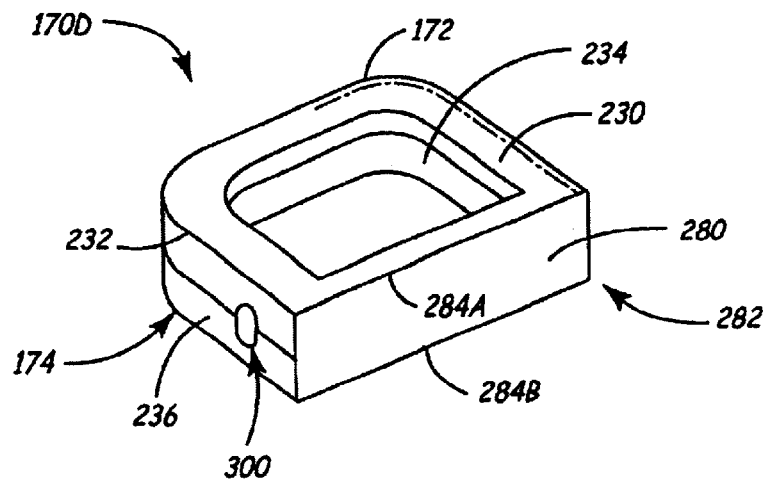

Referring also to FIGS. 18C and 18D, liner 170D is shown in a closed position. In a closed position, fill mechanism 302 is received by notch 304 for securing first part 172 to second part 174 in a closed position. While in a closed position, first outer edge wall 232 and second outer edge wall 236 interact to define an overlapping region 308. Optionally, liner 170 may comprise more than two parts.

Another feature of liner 170 is its use as a stack alignment element. Placement of electrode stack 108 within liner 170 operates to immobilize (the relative orientations of) anode layers 150, cathode layers 152, separator layers 154 and outer separator layers 156 within electrode stack 108 during insertion of electrode stack 108 into case 100. Without liner 170, the layers comprising electrode stack 108 may be prone to sliding or misalignment. As such, liner 170 is sized for a tolerance fit with both case 100 and electrode stack 108, and in one preferred embodiment, liner 170 has the same substantial shape of electrode stack 108. Furthermore, assembly of electrode stack 108 components directly into liner 170 further reduces the probability of layer misalignment in all subsequent operations (wrapping, tab consolidation, tab trimming, tab welding). In one embodiment, outer wrap 158 and wrapping tape 130 are eliminated when electrode assembly 108 is assembled directly into liner 170.

In another alternative embodiment, liner 170 is comprised of flat strips (e.g., a resilient band) around the perimeter edges of electrode stack 108 in conjunction with the use of additional means if necessary, such as taping or tucking, to keep separator layer 154 out of joint 104. Such a liner 170 configuration further decreases the overall thickness of capacitor assembly 64 at the edges.

In a preferred embodiment of the present invention, case liner 170 is formed by a vacuum thermoforming operation. A film of insulative material is heated to its sagging point. The film is mechanically laid onto/into a male or female form, and with the aid of vacuum, formed to the desired liner 170 shape. First part 172 and second part 174 are formed similarly. As the film cools it retains the shape of the forming tool. Forming by this method is done in a single die; alternately, a multiple die set is used. Rough-formed liner 170 is trimmed by die cutting, razor trimming, or equivalent methods in order to provide the final shape. Additional cold forming steps may also be employed to obtain desired features in liner 170 such as the formation cutouts and aperture previously discussed.

Figure 19:
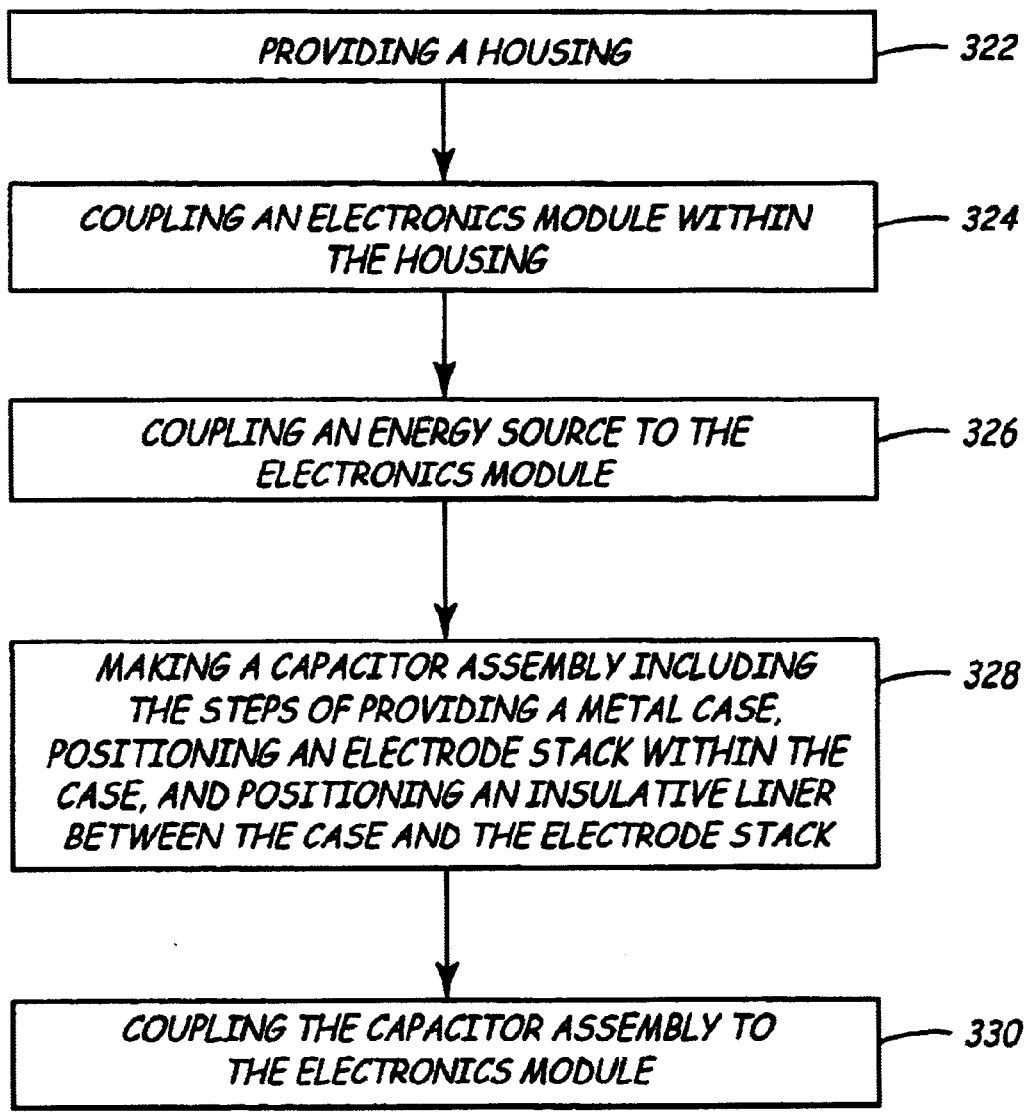
FIG. 19 is a flow chart illustrating one exemplary embodiment of manufacturing an implantable medical device including a capacitor assembly having a liner according to the present invention.

In FIG. 19, a flow diagram illustrating one exemplary embodiment of a method of manufacturing an implantable medical device according to the present invention is generally shown at 320. In step 322, a housing is provided. In step 324, an electronics module is coupled to the housing. In step 326, an energy source is coupled to the electronics module.

In step 328, the method provides for making a capacitor assembly. The step of making a capacitor assembly includes the steps of providing a metal case, positioning an electrode stack within the metal case, and positioning an insulative liner between the case and the electrode stack. The method may further include the step of sealing the capacitor assembly. Additionally, the method may further include the step of thermoforming the insulative liner, which in one aspect, includes the step of thermoforming the insulative liner to substantially the shape of the electrode stack. In another aspect, the method includes the step of coating the insulative liner on an inside surface of the case. In step 330, the capacitor assembly is coupled to the electronics module. Other details for manufacturing and constructing an implantable medical device including a capacitor assembly suitable for use with the present invention are disclosed in U.S. patent application Ser. No. 09/103,638, previously incorporated by reference herein.

The scope of the present invention is not limited to defibrillation or cardioversion applications, or to applications where a human heart is defibrillated, but includes similar applications in other mammalians and mammalian organs. Those of ordinary skill will now appreciate that the method and device of the present invention are not limited to implantable medical devices, but extend to power sources for non-implantable medical devices and for electronic devices generally.

Additionally, although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

We claim:

1. An implantable medical device comprising:
   a housing;
   an electronics module disposed within the housing;
   an energy source electrically coupled to the electronics module; and
   a capacitor assembly disposed within the housing and electrically coupled to the electronics module, the capacitor assembly comprising:
   a case;
   an electrode stack located within the case; and
   an insulative barrier disposed between the case and the electrode stack.

2. The implantable medical device of claim 1 wherein the capacitor assembly insulative barrier is a case liner.

3. The implantable medical device of claim 1 wherein the insulative barrier is constructed of a polymeric material.

4. The implantable medical device of claim 3 wherein the polymeric material is one of polysulfone, polypropylene, polyethylene or EFTE.

5. The implantable medical device of claim 1 wherein the capacitor assembly case is made of an electrically conductive material.

6. The implantable medical device of claim 5, wherein the electrically conductive material is a metal.

7. The implantable medical device of claim 1, wherein the electrode stack includes a cathode layer having an outer edge; an anode layer having an outer edge; and a separator layer having an outer edge, the separator layer disposed between the cathode layer and the anode layer and wherein the insulative barrier is positioned between the case and the outer edge of the cathode layer, the outer edge of the anode layer, and the outer edge of the separator layer.

8. The implantable medical device of claim 7 wherein the outer edge of the separator layer extends beyond the outer edge of the anode layer toward the insulative barrier.

9. The implantable medical device of claim 8, wherein the outer edge of the separator layer extends a maximum 0.100 inches beyond the outer edge of the anode layer.

10. The implantable medical device of claim 9, wherein the outer edge of the separator layer extends 0.5 inches to 0.1 inches beyond the outer edge of the anode layer.

11. The implantable medical device of claim 9, wherein the outer edge of the separator layer extends 0.005 inches to 0.5 inches beyond the outer edge of the anode layer.

12. The implantable medical device of claim 9, wherein the outer edge of the separator layer extends 0.005 inches beyond the outer edge of the anode layer.

13. The implantable medical device of claim 7 wherein the outer edge of the anode layer extends beyond the outer edge of the cathode layer.

14. The implantable medical device of claim 7, wherein the outer edge of the anode layer is substantially aligned with the outer edge of the separator layer.

15. The implantable medical device of claim 7 wherein the outer edge of the separator layer, the outer edge of the anode layer and the outer edge of the cathode layer are substantially aligned.

16. The implantable medical device of claim 1, wherein the capacitor assembly is a substantially flat aluminum electrolytic capacitor assembly.

17. The implantable medical device of claim 16, wherein the capacitor assembly further comprises an electrolyte disposed within the case.

18. The implantable medical device of claim 1, wherein the insulative barrier substantially surrounds the electrode stack.

19. The implantable medical device of claim 18, wherein the insulative barrier includes at least one cutout region.

20. The implantable medical device of claim 19, wherein the liner comprises:

a first major surface;

a second major surface; and an outer edge.

21. The implantable medical device of claim 20, wherein the first major surface has a cutout region.

22. The implantable medical device of claim 20, wherein the outer edge has at least one aperture.

23. The implantable medical device of claim 18, wherein the insulative barrier is tolerance fit to the electrode stack thereby maintaining alignment of the electrode stack.

24. The implantable medical device of claim 1, wherein the shape of the insulative barrier substantially conforms to the shape of the electrode stack.

25. An implantable medical device comprising:

a housing;

an electronics module disposed within the housing;

an energy source electrically coupled to the electronics module; and a capacitor assembly disposed within the housing and electrically coupled to the electronics module, the capacitor assembly comprising:

a case;

an electrode stack located within the case; and a liner made of insulative material substantially surrounding the electrode stack and positioned between the case and the electrode stack.

26. The implantable medical device of claim 22, wherein the liner further comprises a first part and a second part, wherein the electrode stack is positioned between the first part and the second part.

27. The implantable medical device of claim 22, wherein the first part includes a first portion and the second part includes a second portion which overlaps the first portion in an overlap region.

28. The implantable medical device of claim 27, wherein an aperture extends through the overlap region.

29. The implantable medical device of claim 22, wherein the liner further comprises:

a first part having a first substantially planar member and a first outer edge extending substantially perpendicular from the first planar member;

a second part having a second substantially planar member and a second outer edge extending substantially perpendicular from the second major surface; and wherein the electrode stack is positioned between the first part and the second part such that the second outer edge overlaps the first outer edge to form an outer edge assembly.

30. A method of manufacturing an implantable medical device, the method comprising:

providing a housing;

coupling an electronics module within the housing;

coupling an energy source to the electronics module;

making a capacitor assembly including an aspect of providing a metal case, positioning an electrode stack within the case, and positioning an insulative liner between the case and the electrode stack; and coupling the capacitor assembly to the electronics module.

31. The method of claim 30, wherein the method of making the capacitor assembly further comprises the steps of sealing the capacitor assembly.

32. The method of claim 30, further comprising the method of thermoforming the insulative liner.

33. The method of claim 32, wherein the method of thermoforming the insulative liner includes the step of thermoforming the insulative liner to substantially the shape of the electrode stack.

34. The method of claim 30, further comprising the method of coating the insulative liner on an inside surface of the case.

* * * * *

UNITED STATES PATENT AND TRADEMARK OFFICE
CERTIFICATE OF CORRECTION

PATENT NO. : 6,678,559 B1
APPLICATION NO. : 09/531352
DATED : January 13, 2004
INVENTOR(S) : Mark D. Breyen et al.

It is certified that error appears in the above-identified patent and that said Letters Patent is hereby corrected as shown below:

Column 22, line 9, please delete "claim 22" and insert --claim 25--

Column 22, line 13, please delete "claim 22" and insert --claim 25--

Signed and Sealed this

Nineteenth Day of December, 2006

JON W. DUDAS
*Director of the United States Patent and Trademark Office*